US009610425B2

(12) United States Patent
Waters et al.

(10) Patent No.: US 9,610,425 B2
(45) Date of Patent: Apr. 4, 2017

(54) ENDOVENTRICULAR INJECTION CATHETER SYSTEM WITH INTEGRATED ECHOCARDIOGRAPHIC CAPABILITIES

(71) Applicant: ACIST Medical Systems, Inc., Eden Prairie, MN (US)

(72) Inventors: Kendall R. Waters, Livermore, CA (US); Thomas C. Moore, Livermore, CA (US); Robert Zelenka, Milpitas, CA (US); Paul Zalesky, Huntington Beach, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 236 days.

(21) Appl. No.: 14/507,438

(22) Filed: Oct. 6, 2014

(65) Prior Publication Data

US 2015/0025381 A1    Jan. 22, 2015

Related U.S. Application Data

(62) Division of application No. 12/837,770, filed on Jul. 16, 2010, now Pat. No. 8,876,722.
(Continued)

(51) Int. Cl.
*A61B 8/14* (2006.01)
*A61B 8/12* (2006.01)
(Continued)

(52) U.S. Cl.
CPC ....... *A61M 25/0133* (2013.01); *A61B 8/0883* (2013.01); *A61B 8/12* (2013.01);
(Continued)

(58) Field of Classification Search
None
See application file for complete search history.

(56) References Cited

U.S. PATENT DOCUMENTS 5,368,564 A   11/1994   Savage
5,569,219 A   10/1996   Hakki et al.
(Continued)

FOREIGN PATENT DOCUMENTS

WO   WO 00/24448     5/2000
WO   WO03/013625 A2  2/2003

OTHER PUBLICATIONS

English translation of Japanese Patent Publication No. 05-049641, date of publication Mar. 2, 1993, 13 pages.
(Continued)

*Primary Examiner* — Long V Le
*Assistant Examiner* — Bradley Impink
(74) *Attorney, Agent, or Firm* — Fredrikson & Byron, P.A.

(57) ABSTRACT

Methods of providing image-guided transendocardial injection of a therapeutic agent into a left ventricular wall of a heart. Some methods enable injections into heart tissue under visualization. The methods may include providing an endoventricular injection catheter having integrated echocardiographic capability. The endoventricular injection catheter may have an imaging core and an injection system carried on the elongated body with the imaging core. The method may include positioning the endoventricular injection catheter into the left ventricle of the heart, which inserts the imaging core into the heart. The method may also include transmitting ultrasonic energy via the imaging core, receiving reflected ultrasonic energy at the distal end, visualizing the left ventricular wall of the heart using the imaging core, identifying infarct regions of the left ventricle, and injecting a therapeutic agent into the visualized infarcted regions of the left ventricle using the injection system.

11 Claims, 27 Drawing Sheets

Related U.S. Application Data

(60) Provisional application No. 61/228,057, filed on Jul. 23, 2009.

(51) Int. Cl.
*A61B 8/00* (2006.01)
*A61M 25/00* (2006.01)
*A61M 25/01* (2006.01)
*A61B 8/08* (2006.01)
*A61M 25/06* (2006.01)

(52) U.S. Cl.
CPC ............ *A61B 8/445* (2013.01); *A61B 8/5223* (2013.01); *A61M 25/0084* (2013.01); *A61M 25/0662* (2013.01); *A61M 2025/0089* (2013.01); *A61M 2025/0166* (2013.01); *A61M 2025/0175* (2013.01); *A61M 2025/0681* (2013.01); *A61M 2210/125* (2013.01)

(56) References Cited

U.S. PATENT DOCUMENTS

| | | | |
|---|---|---|---|
| 5,797,858 A | 8/1998 | Rourke | |
| 5,845,646 A | 12/1998 | Lemelson | |
| 5,916,209 A | 6/1999 | Mick | |
| 6,004,271 A | 12/1999 | Moore | |
| 6,004,295 A | 12/1999 | Langer et al. | |
| 6,213,974 B1 | 4/2001 | Smith et al. | |
| 6,254,573 B1 * | 7/2001 | Haim | A61M 25/0075 604/157 |
| 6,283,951 B1 * | 9/2001 | Flaherty | A61B 17/11 604/164.11 |
| 6,309,370 B1 | 10/2001 | Haim et al. | |
| 6,361,500 B1 | 3/2002 | Masters | |
| 6,375,615 B1 | 4/2002 | Flaherty et al. | |
| 6,413,222 B1 | 7/2002 | Pantages et al. | |
| 6,511,477 B2 | 1/2003 | Altman et al. | |
| 6,547,787 B1 | 4/2003 | Altman et al. | |
| 6,554,801 B1 | 4/2003 | Steward | |
| 6,589,164 B1 | 7/2003 | Flaherty | |
| 6,592,520 B1 | 7/2003 | Peszynski | |
| 6,641,539 B2 | 11/2003 | Hirooka et al. | |
| 6,645,195 B1 | 11/2003 | Bhat et al. | |
| 6,716,166 B2 | 4/2004 | Govari | |
| 6,773,402 B2 | 8/2004 | Govari | |
| 6,796,963 B2 | 9/2004 | Carpenter et al. | |
| 6,905,476 B2 | 6/2005 | Ponzi | |
| 7,155,272 B2 | 12/2006 | Yamaguchi | |
| 7,258,668 B2 | 8/2007 | Hirooka et al. | |
| 7,402,151 B2 | 7/2008 | Rosenman et al. | |
| 7,500,970 B2 | 3/2009 | Altman | |
| 7,722,549 B2 | 5/2010 | Nakao | |
| 8,170,657 B1 | 5/2012 | Ehrenreich | |
| 2002/0151868 A1 | 10/2002 | Taheri | |
| 2004/0076619 A1 * | 4/2004 | Anversa | A01K 67/0271 424/93.7 |
| 2004/0199115 A1 | 10/2004 | Rosenman | |
| 2004/0208845 A1 * | 10/2004 | Michal | A61K 9/0024 424/78.24 |
| 2005/0065474 A1 | 3/2005 | Larson et al. | |
| 2005/0075574 A1 | 4/2005 | Furnish et al. | |
| 2005/0187519 A1 * | 8/2005 | Harris | A61M 25/0068 604/117 |
| 2006/0036218 A1 | 2/2006 | Goodson, IV et al. | |
| 2006/0142789 A1 | 6/2006 | Lehman et al. | |
| 2006/0210543 A1 * | 9/2006 | Leor | A61K 35/15 424/93.7 |
| 2006/0233850 A1 * | 10/2006 | Michal | A61L 27/20 424/422 |
| 2006/0241342 A1 | 10/2006 | Macaulay et al. | |
| 2007/0016063 A1 | 1/2007 | Park et al. | |
| 2008/0058836 A1 * | 3/2008 | Moll | A61B 1/00082 606/130 |
| 2008/0154217 A1 | 6/2008 | Carrez et al. | |
| 2009/0105597 A1 | 4/2009 | Abraham | |
| 2009/0118700 A1 | 5/2009 | Callas et al. | |
| 2009/0143748 A1 | 6/2009 | Mickley et al. | |
| 2009/0148415 A1 | 6/2009 | de la Fuente et al. | |
| 2009/0156941 A1 | 6/2009 | Moore | |
| 2009/0177093 A1 | 7/2009 | Zelenka et al. | |
| 2010/0152590 A1 * | 6/2010 | Moore | A61B 8/12 600/466 |
| 2010/0298737 A1 | 11/2010 | Koehler | |
| 2011/0276001 A1 | 11/2011 | Schultz et al. | |

OTHER PUBLICATIONS

English translation of Abstract for Japanese Patent Publication No. 2001-104315; date of publication Apr. 17, 2001.
English translation of Abstract for Japanese Patent Publication No. 2005-224445; date of publication Aug. 25, 2005.
International Search Report for International Patent Application No. PCT/US2010/042220, dated Mar. 8, 2011.

* cited by examiner

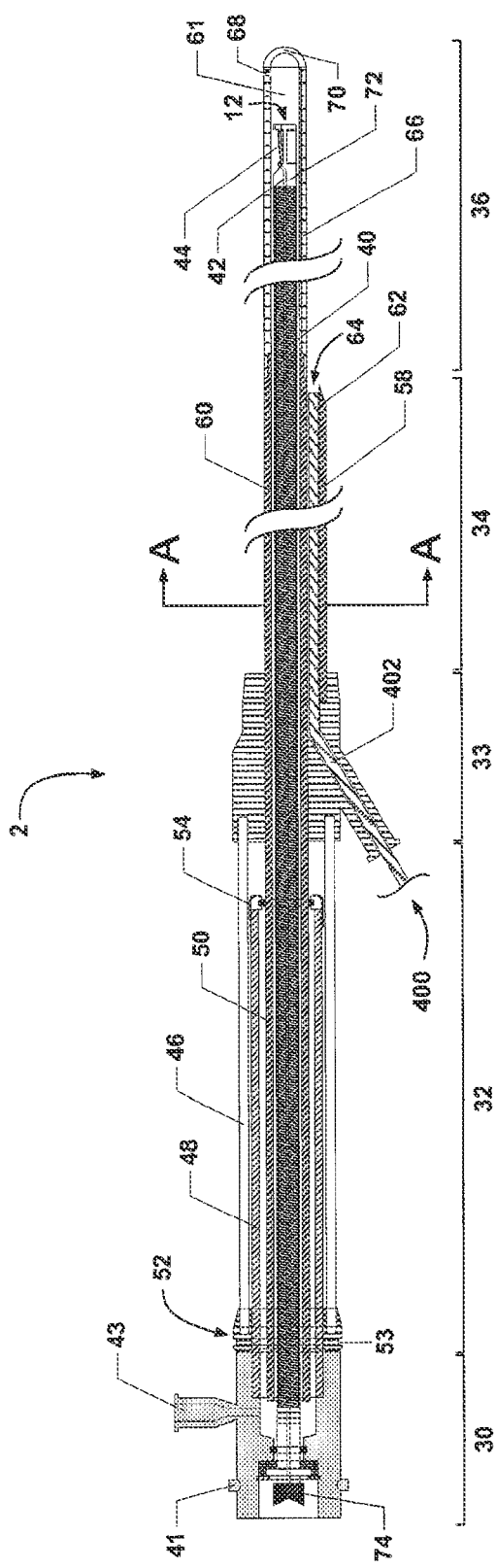
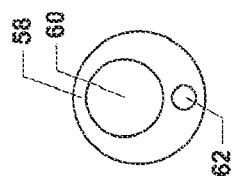
FIG. 3
FIG. 3A

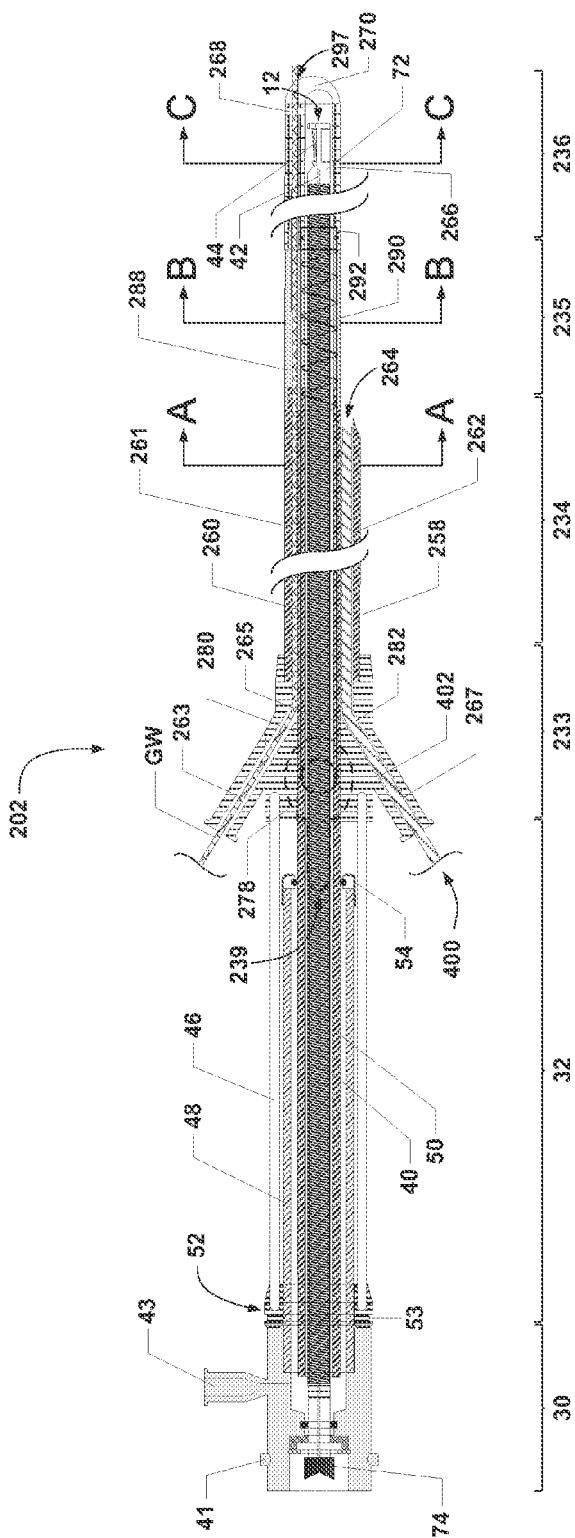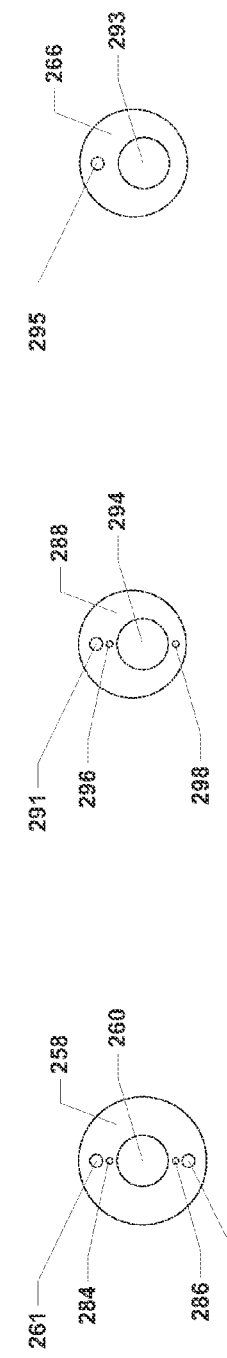
FIG. 7
FIG. 7A
FIG. 7B
FIG. 7C

ENDOVENTRICULAR INJECTION CATHETER SYSTEM WITH INTEGRATED ECHOCARDIOGRAPHIC CAPABILITIES

PRIORITY CLAIM

This application is a divisional application of U.S. patent application Ser. No. 12/837,770, filed Jul. 16, 2010 and titled "ENDOVENTRICULAR INJECTION CATHETER SYSTEM WITH INTEGRATED ECHOCARDIOGRAPHIC CAPABILITIES," which in turn claims the benefit of U.S. Provisional Patent Application Ser. No. 61/228,057, filed Jul. 23, 2009. The entire contents of these applications are incorporated herein by reference in their entirety.

BACKGROUND

The present system generally relates to therapies for patients with heart dysfunction, such as congestive heart failure and other dysfunctions after a heart attack. Some embodiments of the present system more specifically relate to catheter-based therapies for heart dysfunction. Some embodiments of the present system also relate specifically to cell-based therapies for heart dysfunction.

In the United States, there are an estimated 7,750,000 adults that have survived a heart attack, or myocardial infarction. These myocardial infarctions often lead to congestive heart failure and potentially life threatening heart rhythm disorders. Cell-based therapy has emerged as an encouraging approach to rebuilding such damaged hearts. In particular, catheter-based transendocardial injection is considered a promising delivery mode. Examples of therapeutic agents comprise mesenchymal stem cells and skeletal myoblasts.

Effective catheter-based delivery of a therapeutic agent requires knowledge of the internal architecture of the left ventricle and the ability to position and orient the catheter in the left ventricular chamber. Furthermore, the ability to penetrate and inject a therapeutic agent into the myocardium is required, typically by means of an injection needle. It would be advantageous if an endoventricular injection catheter comprised integrated echocardiographic capabilities that enabled real-time image guidance to control depth of needle injection into left ventricular wall and prevent myocardial perforation. It would be further advantageous if the same catheter could be used to identify infarcted regions in order to indicate suitable injection sites. It would be still further advantageous if leakage of the therapeutic agent could be prevented following removal of the injection needle. It would be yet still further advantageous if the therapeutic agent could be delivered from a distal reservoir to minimize trauma to the therapeutic cells during delivery.

SUMMARY OF THE INVENTION

Certain embodiments of the present invention relate to methods of providing image-guided transendocardial injection of a therapeutic agent into a left ventricular wall of a heart. The methods may include providing an endoventricular injection catheter having integrated echocardiographic capability. The endoventricular injection catheter may have an elongated body with a first housing, a second housing and a distal section positioned distal to the second housing in a longitudinal direction. The distal section may have a distal end and an imaging core and an injection system carried on the elongated body with the imaging core. The method may include positioning the endoventricular injection catheter into the left ventricle of the heart, which inserts the imaging core into the heart. The method may also include transmitting ultrasonic energy via the imaging core, receiving reflected ultrasonic energy at the distal end, visualizing the left ventricular wall of the heart using the imaging core, identifying infarct regions of the left ventricle, and injecting a therapeutic agent into the visualized infarcted regions of the left ventricle using the injection system.

BRIEF DESCRIPTION OF THE DRAWINGS

The invention, together with further features and advantages thereof, may best be understood by making reference to the following descriptions taken in conjunction with the accompanying drawings, in the several figures of which like reference numerals identify identical elements, and wherein:

FIG. 3 is a partial sectional view of a catheter embodying aspects of the invention;

FIG. 3A is a sectional view taken along lines A-A of FIG. 3;

FIG. 7 is a partial sectional view of another catheter embodying aspects of the invention;

FIG. 7A is a sectional view taken along lines A-A of FIG. 7;

FIG. 7B is a sectional view taken along lines B-B of FIG. 7;

FIG. 7C is a sectional view taken along lines C-C of FIG. 7;

DETAILED DESCRIPTION OF THE EMBODIMENTS

Figure 1:
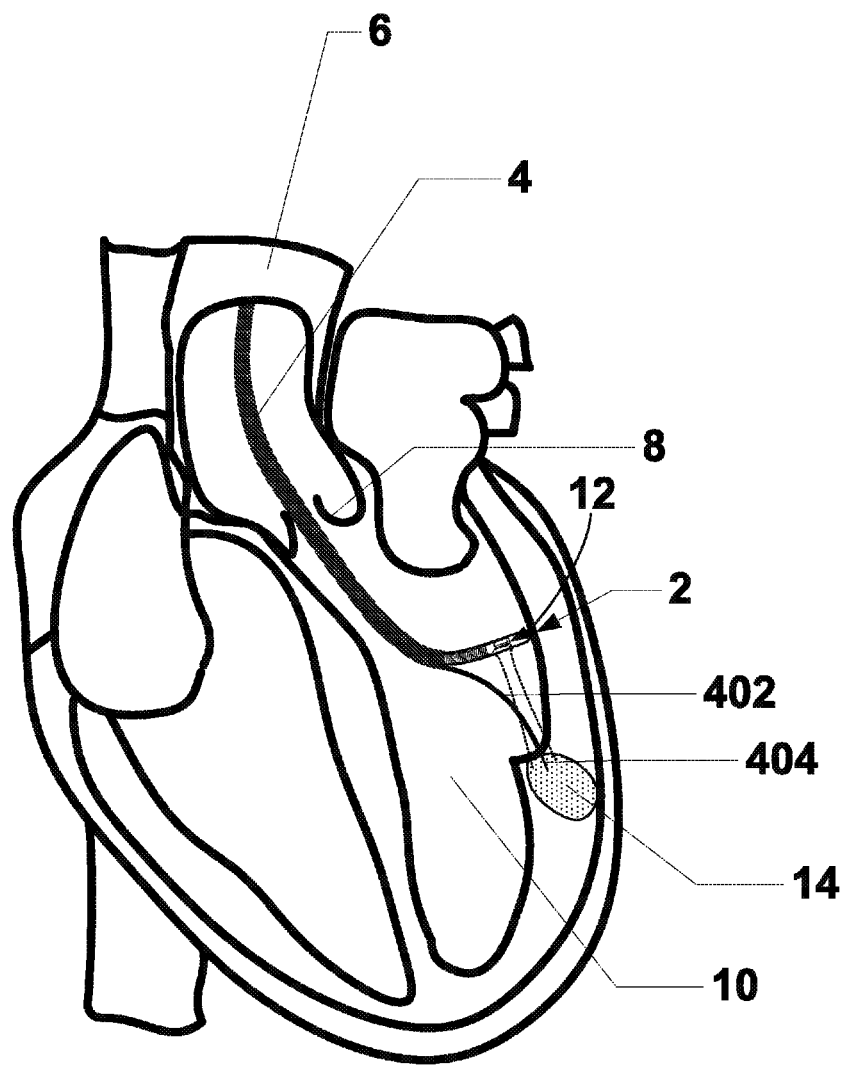
FIG. 1 illustrates use of catheter.

FIG. 1 shows a cut-away illustration of a heart having therein an endoventricular injection catheter 2 having integrated echocardiographic capabilities delivered via a steerable guide sheath 4. The steerable guide sheath 4 is delivered percutaneously from a femoral arterial site to the aorta 6 and through the aortic valve 8 into the left ventricle 10. The catheter 2 comprises a mechanically rotating imaging core 12, an injection cannula 402, and an injection needle 404. FIG. 1 illustrates how the steerable guide sheath 4 and endoventricular injection catheter 2 can be used to inject a needle into a region of interest 14 in the left ventricular wall under echocardiographic guidance.

Figure 2:
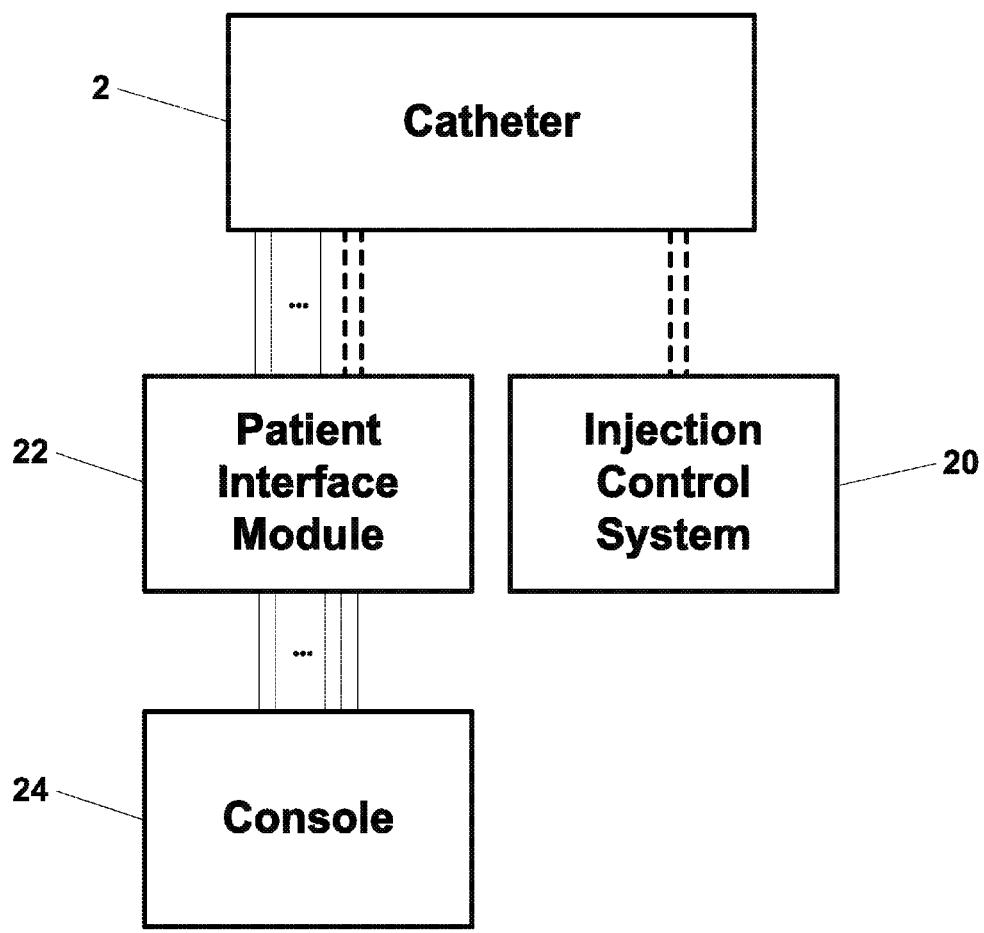
FIG. 2 shows a block diagram of an endoventricular injection catheter system with integrated echocardiographic capabilities.

FIG. 2 shows a high-level block diagram of the endoventricular injection catheter system comprising the endoventricular injection catheter 2 with integrated echocardiographic capabilities, an injection control system 20, a patient interface module 22, and console 24. The injection control system 20 is mechanically coupled to the catheter 2. The patient interface module is electrically and mechanically coupled to the catheter. The patient interface module 22 further provides electrical isolation of the patient from the system. The patient interface module 22 may take the form as described for example in additional detail in U.S. patent application Ser. No. 12/633,278 by Moore et al., the complete disclosure of which is hereby incorporated herein by reference. The patient interface module 22 and console 24 are coupled by analog and digital signal lines. The console 24 controls operation of the patient interface module 22 and the imaging aspect of the catheter 2. The console 24 may further display images. The endoventricular injection catheter system may be employed to advantage to provide, for example, image guidance of transendocardial injection of therapeutic agents such as cell-based solutions to heart attack victims.

Referring to FIG. 3, it shows an endoventricular injection catheter with integrated echocardiographic capability 2 embodying aspects of the present invention. The catheter 2 comprises a first proximal housing 30, a telescoping section 32, a second proximal housing 33, a proximal section 34, a distal section 36, an imaging core 12, and an injection system 400. The endoventricular injection catheter 2 may be used in combination with a steerable guide sheath 4 (FIG. 1) wherein the catheter 2 is disposed within the steerable guide sheath 4 as illustrated in FIG. 1. The catheter length may be generally between 100 cm and 150 cm, more particularly, for example, between 110 cm and 120 cm. The diameter of the catheter proximal section 34 may generally be between 8 F and 18 F, as for example approximately 10 F. The diameter of the catheter distal section 36 may be between 6 F and 10 F, as for example about 8 F.

The first proximal housing 30 mates to the patient interface module (not shown) via engagement pins 41 and couples mechanical energy to the drive cable 40 and electrical energy into a transmission line 42 disposed within the drive cable 40 that is electrically connected to the ultrasonic transducer 44. A saline flush port 43 enables acoustic coupling from the ultrasonic transducer 44 to the exterior of the distal section 36. For additional description of the first proximal housing 30, reference may be had for example, to U.S. patent application Ser. No. 12/336,441 by Moore the complete disclosure of which is hereby incorporated herein by reference.

The telescoping section 32 enables longitudinal translation of the imaging core 12 with respect to the catheter sheaths. The telescoping section 32 includes an outer supporting member 46, an inner tubular member 48, and a primary inner member 50 that slides into the inner tubular member 48. The telescoping section further includes an end cap 52 and an end stop 54 that is bonded to the distal end of the inner tubular member 48. The inner tubular member 48 is bonded to the proximal housing 30. The supporting member 46 and the primary inner member 50 are bonded to the second proximal housing 33. The end cap 52 includes a groove 53 that provides a connection point for controlled movement of the telescoping section 32. The end stop 54 prevents the supporting member 46 and primary inner member 50 from disengaging the inner tubular member 48 when the telescoping section is fully extended. The telescoping section length is generally between 1 cm and 5 cm, more particularly between 2 cm and 3 cm. The primary inner member 50 is formed of a biocompatible material such as polyetheretherketone (PEEK) or stainless steel. The primary inner member 50 has an inner diameter typically between 0.075" and 0.100". The supporting member 46 is also formed of a biocompatible material such as PEEK or stainless steel. Further description of such a telescoping section may be found, for example, in U.S. patent application Ser. No. 12/336,441 by Moore, the complete disclosure of which is hereby incorporated herein by reference.

The proximal section 34 includes a secondary member 58, an imaging core lumen 60, and an injection cannula lumen 62. A cross-sectional view of the proximal section 34 is illustrated in FIG. 3A. The proximal section 34 further includes an exit port 64 for the injection cannula. The secondary member 58 is formed of a biocompatible flexible material such as PEEK and has an outer diameter generally between 8 F and 18 F, more particularly approximately 10 F. The imaging core lumen 60 diameter may be between 0.075" and 0.100". The injection cannula lumen 62 diameter may be between 0.030" and 0.037", sufficient to pass an injection cannula of size typically between 20 gauge to 22 gauge.

The distal section 36 includes a distal sheath 66, a flushing exit port 68, an atraumatic tip 70, and an imaging core lumen 61. The distal sheath 66 is formed of a biocompatible flexible material such as polyethylene or other thermoplastic polymer that minimizes acoustic loss. The atraumatic tip 70 is formed of a low durometer material such as polyether block amide (Pebax®) or blend of Pebax grades such as Pebax 63D and 40D. The imaging core lumen 60 diameter may be between 0.075" and 0.100".

The imaging core 12 includes a drive cable 40, a transducer housing 72, an ultrasonic transducer 44, and a transmission line 42 disposed within the drive cable 40. The imaging core is electrically and mechanically coupled by a connector 74 to the patient interface module. The electrical coupling enables sending and receiving of electrical signals along the transmission line 42 to the ultrasonic transducer 44. The mechanical coupling enables rotation of the imaging core 12. The drive cable 40 may be formed of a stainless steel round-wire coil with a coil outer diameter in the range 0.070" to 0.180", more particularly approximately 0.105" for a 10 F distal sheath profile. The elongation and compression of the drive cable during acceleration must be minimized to insure accurate positioning. The drive cable should also minimize nonuniform rotation of the imaging core. The transducer housing 72 is described in additional detail in U.S. patent application Ser. No. 12/330,308 by Zelenka and Moore, the complete disclosure of which is hereby incorporated herein by reference.

The ultrasonic transducer 44 includes at least a piezoelectric layer and may further include conductive layers, at least one matching layer, and a backing layer. The ultrasonic transducer 44 may further include a lens. Design and fabrication of ultrasonic transducers for imaging catheters are known to those skilled in the art. The ultrasonic transducer generally operates over frequency ranges of 5 MHz to 60 MHz, more particularly between 10 MHz to 30 MHz.

The injection system 400 comprises an injection cannula 402 and an injection needle (not shown) disposed within the injection cannula 402. The injection cannula 402 may be formed of a biocompatible superelastic material such as a nickel-titanium (or Nitinol) alloy that can take a curved shape. The cannula size is generally between 20 gauge and 24 gauge, more particularly approximately 22 gauge. The distal tip of the injection cannula 402 can be treated to be echogenic to facilitate ultrasound image guidance.

Figure 4:
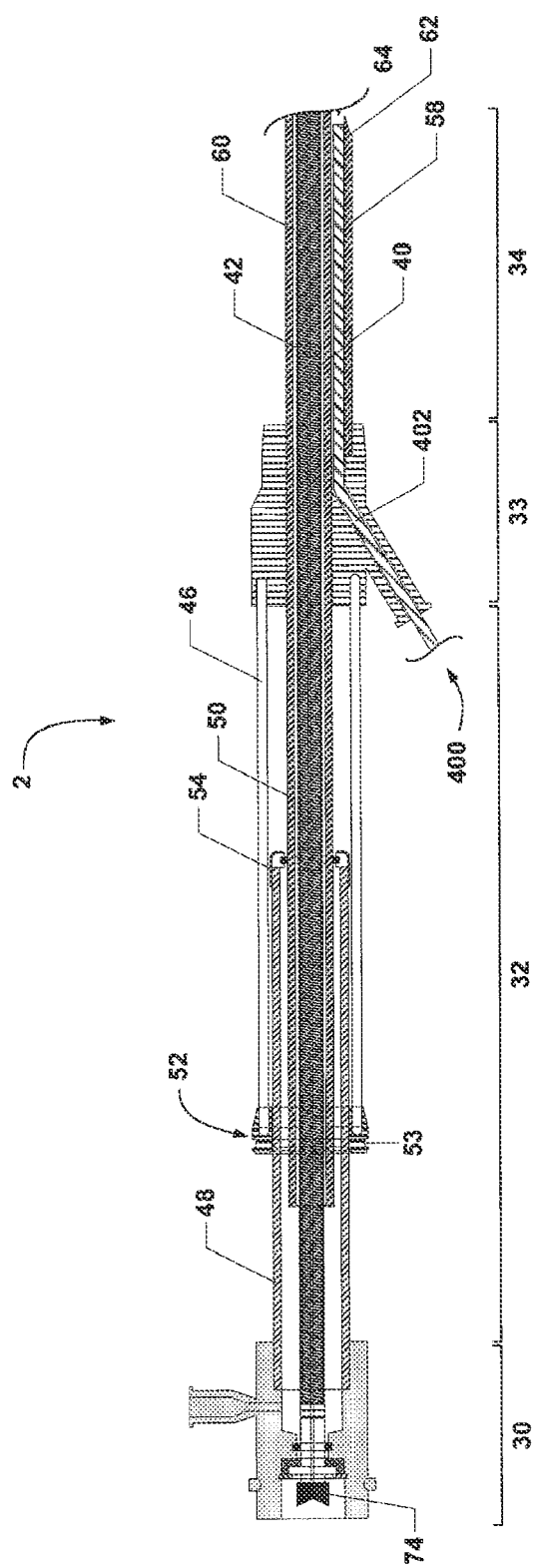
FIG. 4 is a partial sectional view of the catheter of FIG. 3 shown partially extended.

FIG. 4 illustrates the endoventricular injection catheter 2 of FIG. 3 with the telescoping section 32 in a partially extended position. The first proximal housing 30 and imaging core 12 which are fixedly attached to each other are shown translated relative to the telescoping section 32, the second proximal housing 33, and the proximal sheath 34. Telescoping imaging catheters enable the imaging core 12 to translate longitudinally through the imaging core lumen 60 while the proximal sheath 34 and distal sheath (not shown) remain fixed in position. As described herein, the imaging core 12 can translate longitudinally through the imaging core lumen 60. The position of the imaging core 12 when the telescoping catheter 32 is in an un-extended state is shown in FIG. 3. The distance of travel of the imaging core 12 between the un-extended position and the fully-extended position within the length of the inner tubular member is limited by end stop 54. As mentioned elsewhere herein, the end cap 52 facilitates controlled movement of the telescoping section 32 and the end stop 54 prevents the supporting member 46 and primary inner member 50 from disengaging the inner tubular member 48 when the telescoping section is fully extended.

Figure 5:
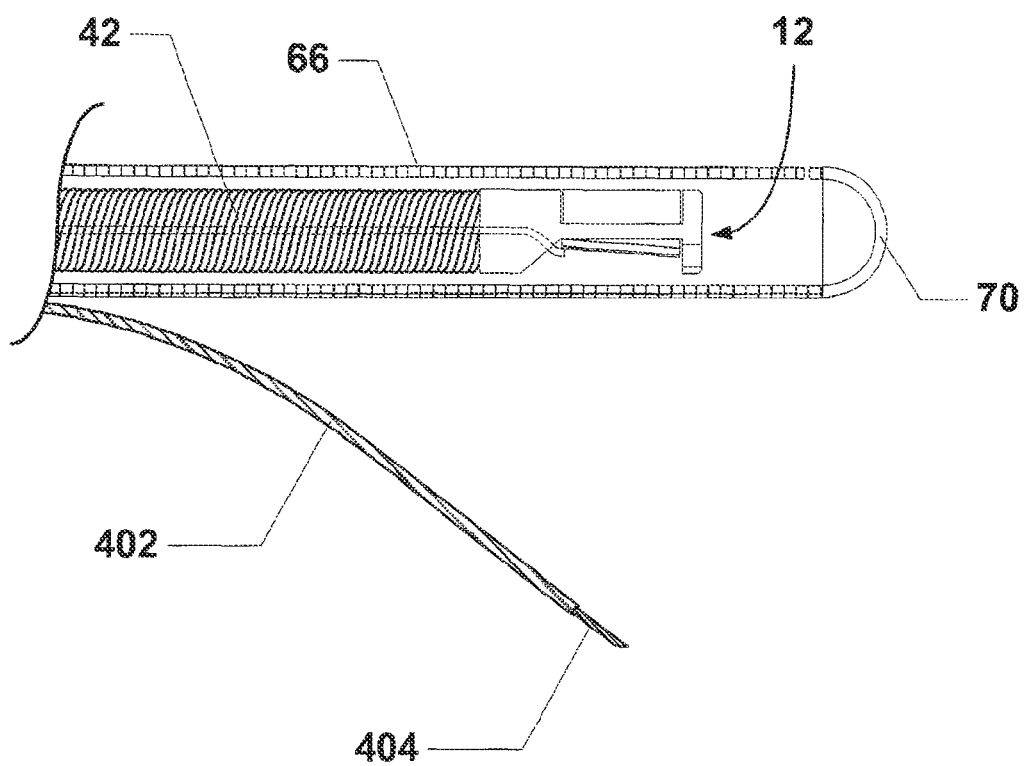
FIG. 5 is a partial sectional view of the distal end of the catheter of FIG. 3 having an injection cannula and needle according to an aspect of the present invention.

FIG. 5 illustrates the distal end of the embodiment of FIG. 3 for echocardiographic guidance of the injection cannula 402 and an injection needle 404. The injection cannula 402 is shaped to facilitate image-guided delivery of the injection needle 404 to a specific site of interest. The optimal bend angle for image guidance of transendocardial injections can be determined empirically. An endoventricular injection catheter with integrated echocardiographic capabilities provides real-time image guidance during needle injection into the left ventricular wall and facilitates prevention of myocardial perforation.

Figure 6:
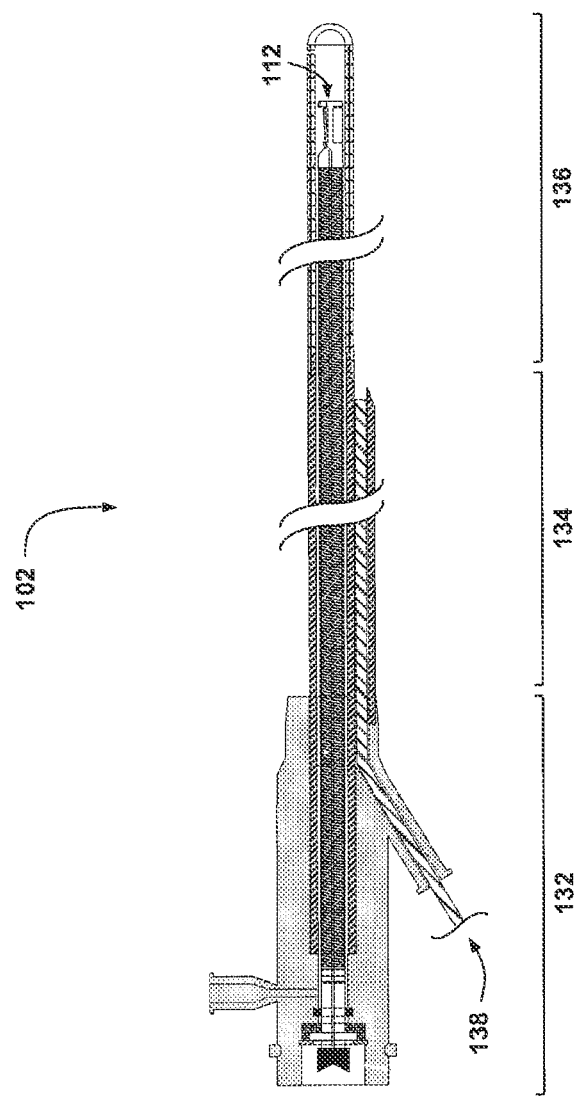
FIG. 6 is a partial sectional view of another catheter embodying the present.

Referring now to FIG. 6, another endoventricular injection catheter 102 with integrated echocardiographic capabilities embodying aspects of the invention is shown. The endoventricular injection catheter 102 comprises a proximal housing 132, a proximal member 134, a distal sheath 136 and an injection system 138. The longitudinal position of the imaging core 112 remains fixed relative to the catheter sheaths 134, 136 because no telescoping section is included. A non-telescoping catheter may be advantageous because of reduced complexity and manufacturing cost in applications wherein longitudinal positioning of the imaging core 112 is not critical.

Referring to FIG. 7, another alternative embodiment of an endoventricular injection catheter 202 with integrated echocardiographic and deflection capabilities embodying aspects of the invention is shown. The endoventricular injection catheter 202 includes the first proximal housing 30, the telescoping section 32, a second proximal housing 233, a proximal section 234, a deflection section 235, a distal section 236, the imaging core 12, the injection system 400, and a deflection control system 239. An advantage of an endoventricular injection catheter with a deflection capability is a steerable guide sheath is not required for delivery and positioning of the catheter. The catheter length may be generally between 100 cm and 150 cm, more particularly between 110 cm and, for example 120 cm. The diameter of the proximal section 234 may be generally between 8 F and 18 F, more particularly, for example, approximately 10 F. The diameter of the distal section 236 may be generally between 6 F and 10 F, more particularly, for example, approximately 8 F.

The first proximal housing 30 mates to the patient interface module (not shown) via engagement pins 41. It couples mechanical energy to the drive cable 40 and electrical energy into a transmission line 42 disposed within the drive cable 40 that is electrically connected to the ultrasonic transducer 44.

The telescoping section 32, as previously described enables longitudinal translation of the imaging core 12 with respect to the catheter sheaths. The telescoping section 32 includes the outer supporting member 46, the inner tubular member 48, and the primary inner member 50 that slides into the inner tubular member 48. The telescoping section further includes the end cap 52 and an end stop 54 that is bonded to the distal end of the inner tubular member 48. The inner tubular member 48 is bonded to the proximal housing 30. The supporting member 46 and the primary inner member 50 are bonded to the second proximal housing 33. The end cap 52 includes a groove 53 that provides a connection point for controlled movement of the telescoping section 32. The end stop 54 prevents the supporting member 46 and primary inner member 50 from disengaging the inner tubular member 48 when the telescoping section is fully extended. The telescoping section length may be generally between 1 cm and 5 cm, more typically between 2 cm and 3 cm. The primary inner member 50 may be formed of a biocompatible material such as polyetheretherketone (PEEK) or stainless steel. The primary inner member 50 an inner diameter typically between 0.075" and 0.100", for example. The supporting member 46 may also be formed of a biocompatible material such as PEEK or stainless steel.

The second proximal housing 233 includes a guide wire lumen 263, an imaging core lumen 265, and an injection cannula lumen 267. The second proximal housing 233 further includes a deflection control knob 278 that is bonded to steering wires 280, 282, as by welding, brazing, or soldering, for example. The second proximal housing 233 may be formed of a biocompatible rigid material. The guide wire lumen 263 diameter may be between 0.015" and 0.037", sufficient, for example, to pass 0.014", 0.018" and 0.035" guide wires. The imaging core lumen 265 diameter may be between 0.075" and 0.100". The injection cannula lumen 267 diameter may be between 0.030" and 0.037", sufficient, for example, to pass an injection cannula of size generally between 20 gauge to 22 gauge. The second proximal housing 233 is bonded to the primary inner member 50 and a secondary member 258 of the proximal section 234.

Referring now to FIG. 7A along with FIG. 7, the proximal section 234 includes the secondary member 258 and multiple lumens. The multiple lumens include an imaging core lumen 260, a guide wire lumen 261, an injection cannula lumen 262, and two steering wire lumens 284, 286. The proximal section further includes an exit port 264 for the injection cannula. The secondary member 258 may be formed of a biocompatible flexible material such as PEEK and may have an outer diameter generally between 8 F and 18 F, more particularly approximately 10 F, for example. The diameter of the imaging core lumen 260 may be between 0.075" and 0.100". The diameter of the guide wire lumen 261 may be between 0.015" and 0.037", sufficient, for example, to pass 0.014", 0.018" and 0.035" guide wires. The diameter of the steering wire lumen 284, 286 may be between 0.008" and 0.014", sufficient, for example, to pass a steering wire having a diameter of between 0.006" and 0.012", for example. The diameter of the injection cannula lumen 262 may be between 0.030" and 0.037", sufficient, for example, to pass an injection cannula of size between 20 gauge to 22 gauge, for example.

Referring now to FIG. 7B along with FIG. 7, the deflection section 235 includes a deflection section sheath 288, reinforcement coil 290, a steering ring 292, and multiple lumens. The deflection section sheath 288 may be formed of a low durometer material such as an olefin. Olefins facilitate bonding to the proximal section 234 and distal section 236. The use of a low durometer material further insures that the catheter bends in the deflection section 235. The multiple lumens include an imaging core lumen 294, a guide wire lumen 291, and two steering wire lumens 296, 298. The diameter of the imaging core lumen 294 may be between 0.075" and 0.100". The diameter of the guide wire lumen 291 may be between 0.015" and 0.037", sufficient, for example, to pass 0.014", 0.018" and 0.035" guide wires. The diameter of the two steering wire lumens 296, 298 may be between 0.008" and 0.014", sufficient, for example, to pass a steering wire having a diameter between 0.006" and 0.012", for example.

Referring now to FIG. 7C along with FIG. 7, the distal section 236 includes a distal sheath 266, a flushing exit port 268, an atraumatic tip 270, an imaging core lumen 293, and a guide wire lumen 295. The distal section further includes an exit port 297 for the guide wire. The distal sheath 266 may be formed of a biocompatible flexible material such as polyethylene or other thermoplastic polymer that minimizes acoustic loss. The atraumatic tip may be formed of a low durometer material such as polyether block amide (Pebax®) or blend of Pebax grades such as Pebax 63D and 40D. The diameter of the imaging core lumen 293 may be between 0.075" and 0.100". The diameter of the guide wire lumen 295 may be between 0.015" and 0.037", sufficient, for example, to pass 0.014", 0.018" and 0.035" guide wires.

The imaging core 12 includes a drive cable 40, a transducer housing 72, an ultrasonic transducer 44, and the transmission line 42 disposed within the drive cable 40. The imaging core is electrically and mechanically coupled by a connector 74 to the patient interface module. The electrical coupling enables sending and receiving of electrical signals along the transmission line 42 to the ultrasonic transducer 44. The mechanical coupling enables rotation of the imaging core 12. The drive cable 40 may be formed of a stainless steel round-wire coil having a coil outer diameter in the range 0.070" to 0.180", for example, approximately 0.105" for a 10 F distal sheath profile. The elongation and compression of the drive cable during acceleration must be minimized to insure accurate positioning. The drive cable should also minimize non-uniform rotation of the imaging core. The transducer housing 72 is described in additional detail in U.S. patent application Ser. No. 12/330,308 by Zelenka and Moore the complete disclosure of which is hereby incorporated herein by reference.

The ultrasonic transducer 44 may include at least a piezoelectric layer and typically further comprises conductive layers, at least one matching layer, and a backing layer. The ultrasonic transducer 44 may further comprise a lens. Design and fabrication of ultrasonic transducers for imaging catheters are known to those skilled in the art. The ultrasonic transducer generally operates over frequency ranges of 5 MHz to 60 MHz, more typically between 10 MHz to 30 MHz.

The injection system 400 includes an injection cannula 402 and an injection needle (not shown) disposed within the injection cannula 402. The injection cannula 402 may be formed of a biocompatible superelastic material such as a nickel-titanium (or Nitinol) alloy that can take a curved shape. The cannula size may be between 20 gauge and 24 gauge, more particularly approximately 22 gauge, for example. The distal tip of the injection cannula 402 can be treated to be echogenic to facilitate ultrasound image guidance.

Figure 8:
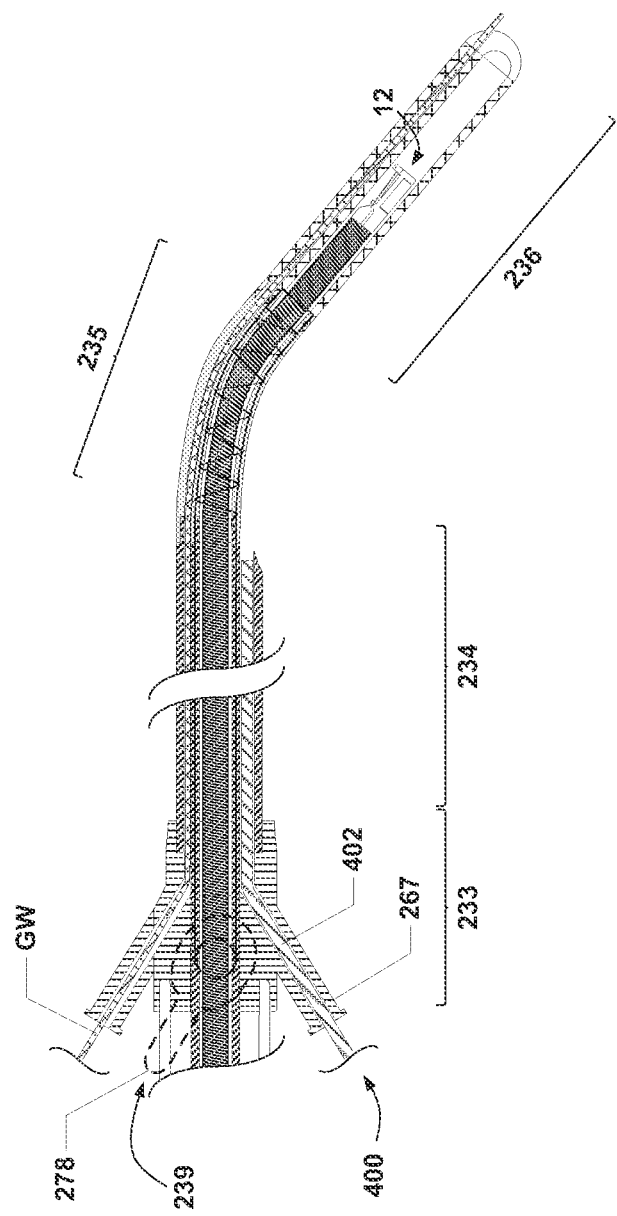
FIG. 8 is a partial sectional view of another catheter embodying aspects of the invention, shown deflected.

The deflection system 239 generally includes deflection control means, at least one steering wire, and a steering ring. In accordance with this embodiment, the deflection system 239 includes a deflection control knob 278, two steering wires 280, 282, and a steering ring 292. The steering wires may be formed of polytetrafluoroethylene (PTFE) coated stainless steel. The diameter of the steering wires 280, 282 may be between 0.006" and 0.012". The steering wires 280, 282 may be welded, brazed, or soldered to the steering ring 292. The steering ring 292 may be formed of stainless steel and located toward the distal end of the deflection section 235. The reinforcement coil 290 of the deflection section 235 prevents pinching of the imaging core lumen 294. Alternatively, a reinforcement braid could be used in place of the reinforcement coil. The location of the injection cannula exit port 264 proximal to the deflection section 235 insures that the injection cannula 402 does not prevent deflection of the catheter. FIG. 8 illustrates deflection of the distal end of the endoventricular injection catheter 202 when the deflection control knob 278 is rotated.

Figure 9:
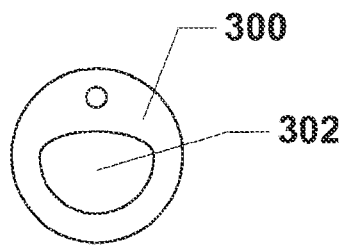
FIG. 9 is a sectional view of still another catheter embodying aspects of the invention.

An over-the-wire imaging catheter sheath having variable thickness between the outer diameter and the imaging core lumen can lead to imaging artifacts. A distal section sheath 300 having an alternative imaging core lumen 302 as illustrated in FIG. 9 provides a more uniform sheath thickness in the lower portion of the sheath which is relevant to the imaging direction.

Figure 10:
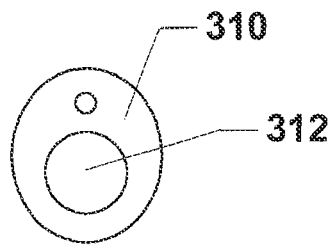
FIG. 10 is a sectional view of still another catheter embodying aspects of the invention.
Figure 11:
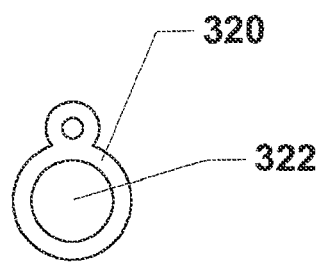
FIG. 11 is a sectional view of still another catheter embodying aspects of the invention.

Another alternative embodiment of the distal section has an elliptical-shaped sheath 310 as illustrated in FIG. 10 with an alternative imaging core lumen 312. It also provides a more uniform sheath thickness in the lower portion of the sheath. Still another embodiment of the distal section is shown in FIG. 11 wherein the distal sheath 320 provides for a still larger range of directions having a uniform sheath thickness. FIG. 11 shows an alternate embodiment of the image core lumen 322.

Short monorail tip catheter designs provide an alternative to over-the-wire catheter designs wherein a short monorail tip enables rapid exchange of the catheter in comparison to the over-the-wire design shown in FIG. 7. An advantage of rapid exchange catheters is that they typically have smaller overall profiles compared to over-the-wire catheters. Catheters having smaller profiles require smaller access sites, such as the femoral artery, which may in turn reduce bleeding complications. With a monorail design it is not necessary to have a guide wire lumen in the deflection control section, proximal section, deflection section, or distal sheath. The reduction in material can reduce the cost of manufacturing.

Figure 12:
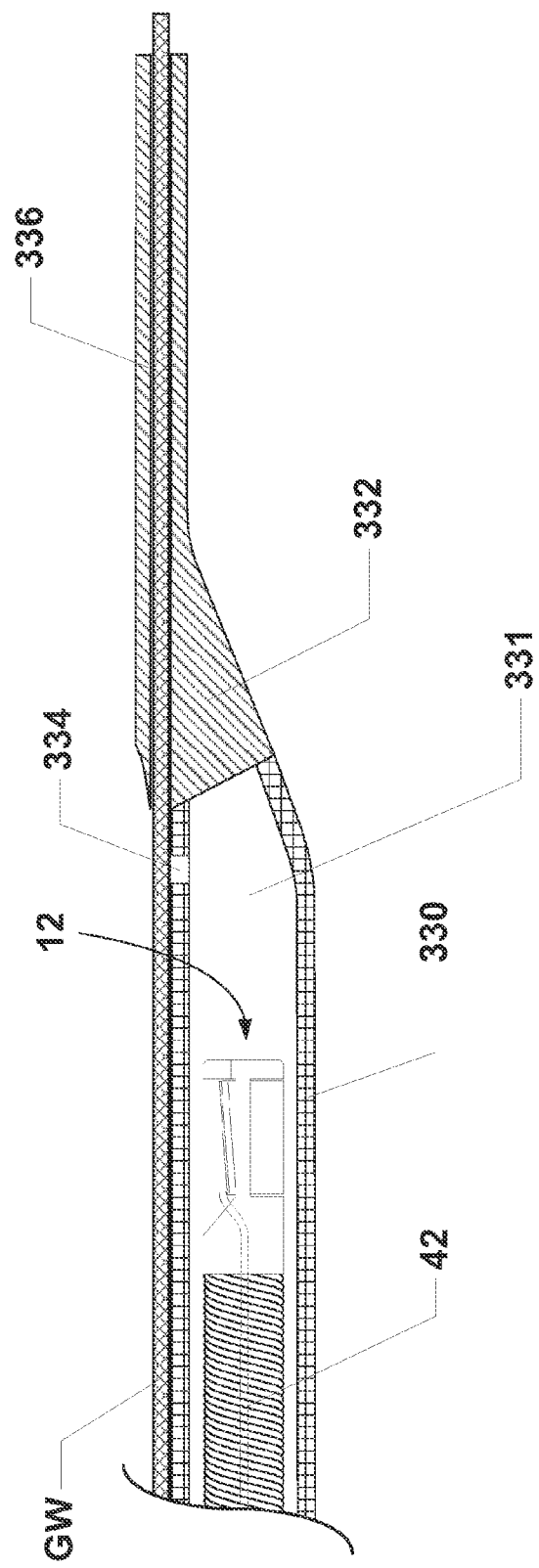
FIG. 12 is a partial sectional view of the distal end of another catheter embodying aspects of the invention.

FIG. 12 illustrates an alternative embodiment of the distal section including a distal sheath 330 having an imaging core lumen 331, a short monorail tip 332, a flushing exit port 334, and a guidewire lumen 336 for guidewire GW. The short monorail tip 332 is bonded to the distal sheath 330 wherein the imaging core lumen 331 is parallel to the guide wire lumen 336. The wall thickness in the distal sheath 330 is uniform around the imaging core lumen 331. Such a distal section including a monorail design is described, for example, in additional detail in U.S. patent application Ser. No. 12/547,972 by Zelenka the complete disclosure of which is hereby incorporated by reference.

Figure 13:
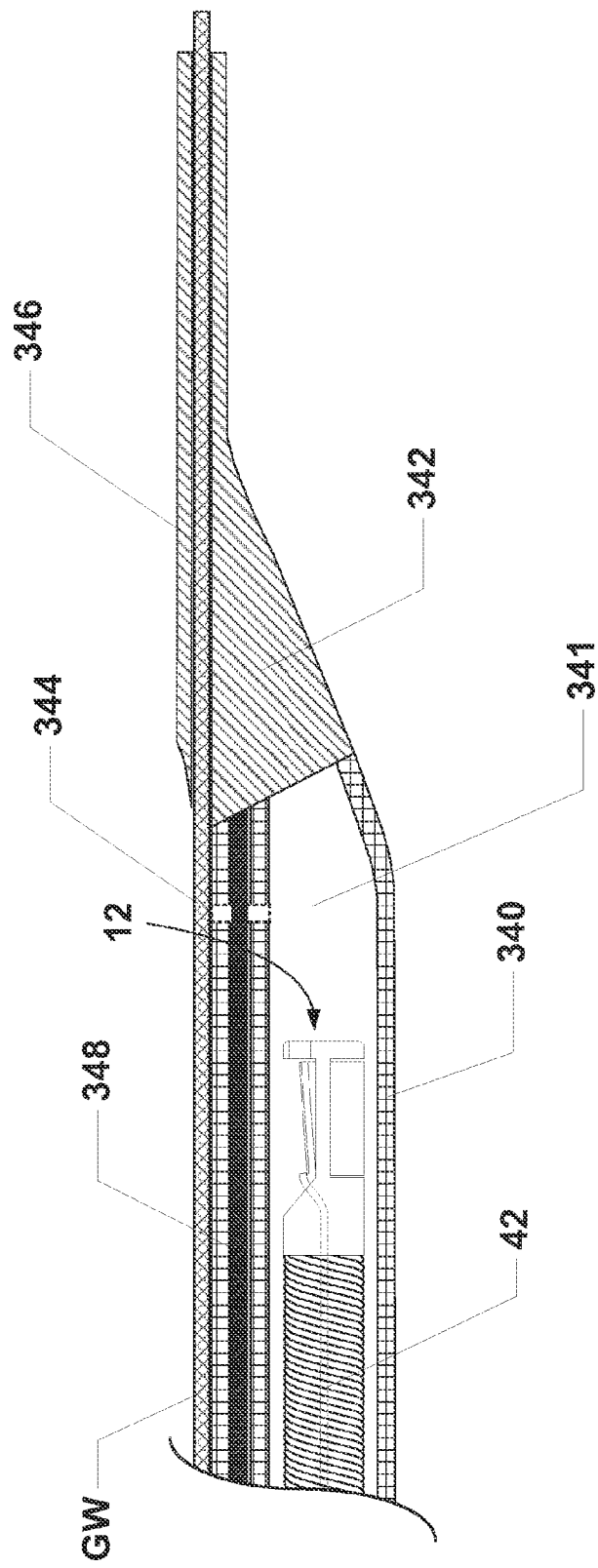
FIG. 13 is a partial sectional view of the distal end of another catheter embodying aspects of the invention.

FIG. 13 illustrates another alternative distal section embodiment including a distal sheath 340 having an imaging core lumen 341, a short monorail tip 342, a flushing exit port 344, a guidewire lumen 346 for guidewire GW, and a support bar 348. The support bar 348 can prevent collapse of the imaging core lumen 341 in cases of large deflections of the catheter. The support bar 348 is formed of a suitably rigid material such as stainless steel or PEEK.

An advantage of an imaging catheter with a mechanically rotating and translating imaging core is the ability to image a volume of interest without repositioning the catheter sheath. The imaging core can be longitudinally translated within the catheter sheath by means of an external translation device. A disadvantage of an imaging catheter with a mechanically rotating and translating imaging core for imaging moving structures such as the heart is that the rate at which a volume can be swept is relatively slow compared to cardiac motion velocities. Imaging cores comprising multiple transducer elements can reduce the time to image a volume of interest.

Figure 14:
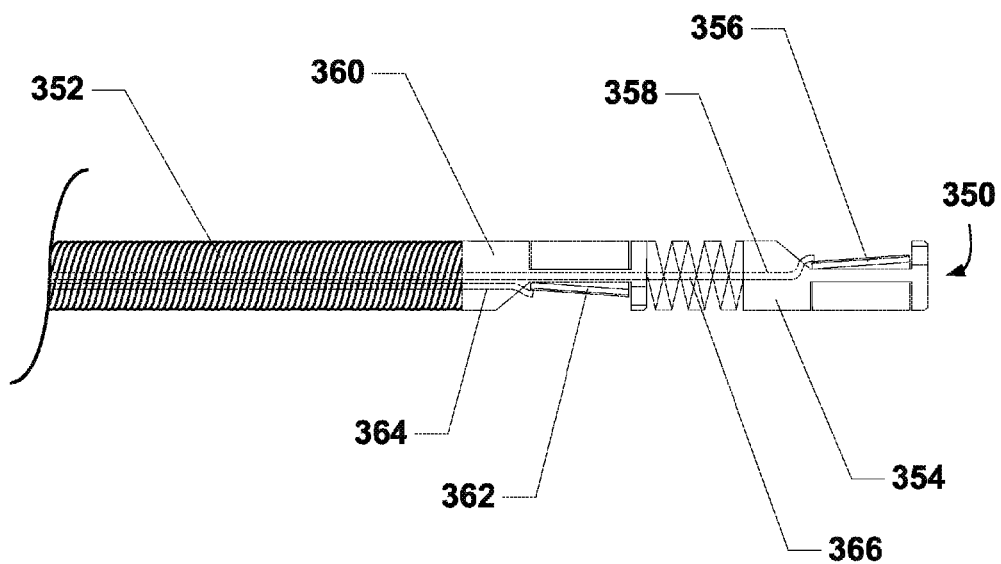
FIG. 14 is a side view of an imaging core of another catheter having multiple transducers according to further aspects of the invention.

FIG. 14 illustrates an alternative embodiment of an imaging core 350 including a drive cable 352, a first transducer housing 354, a first ultrasonic transducer 356, a first transmission line 358, a second transducer housing 360, a second ultrasonic transducer 362, a second transmission line 364, and a transducer housing coupling 366. The first ultrasonic transducer 356 is seated in the first transducer housing 354 and is connected to the first transmission line 358. The second ultrasonic transducer 362 is seated in the second transducer housing 360 and is connected to the second transmission line 364. The facing direction of the second transducer housing 360 and second ultrasonic transducer 362 is 180° relative to the facing direction from the facing direction of the first transducer housing 354 and first ultrasonic transducer 356. The first transducer housing 354 and second transducer housing 360 are mechanically connected by the transducer housing coupling 366, generally a flexible coil.

The use of multiple transducers reduces the amount of time required to ultrasonically scan a volume. In an exemplary design, the first and second transducer housings 354, 360 and transducer housing coupling 366 can be fabricated from a single stainless steel hypotube. The first and second transducer housings 354, 360 provide rigid support to the first and second ultrasonic transducers 356, 362 by means of a fitted slot. The transducer housing coupling 366 is a spiral-cut section of the hypotube and balances axial rigidity to the first and second transducer assemblies with bending flexibility. The pitch of the spiral cut can be constant or can be varied depending upon the target stiffness characteristics. For example, the pitch may be decreased for more flexibility or increased for less flexibility. In an exemplary design, the first and second transducer housings 354, 360 may be approximately 0.155" in length, the transducer housing coupling 366 may be approximately 0.235" in length, and the transducer diameters may be 0.100", for example. The pitch of spiral-cut coupling may be 0.040" having 0.004" kerfs. The alternative embodiment of an imaging core comprising multiple transducers is described in additional detail in U.S. patent application Ser. No. 12/633,278 by Moore et al. the complete disclosure of which is hereby incorporated by reference.

Figure 15A:
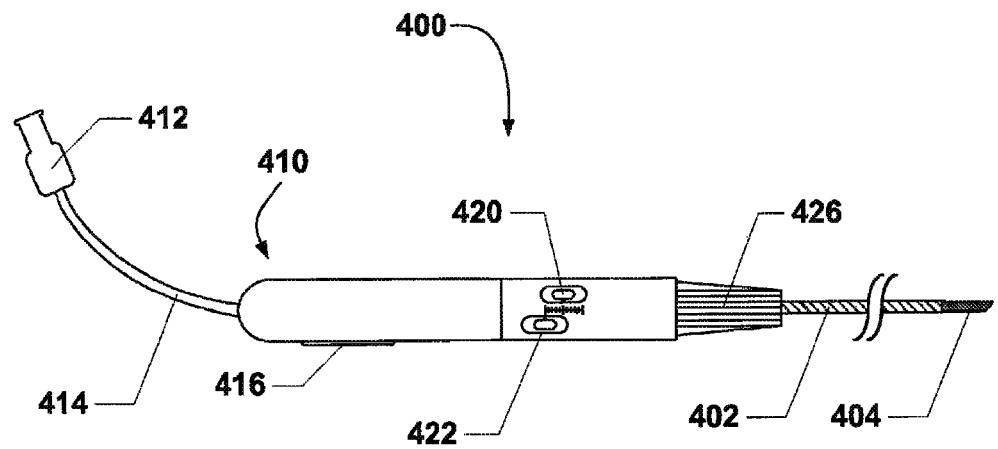
FIG. 15A is a top view of an injection system embodying aspects of the invention.
Figure 15B:
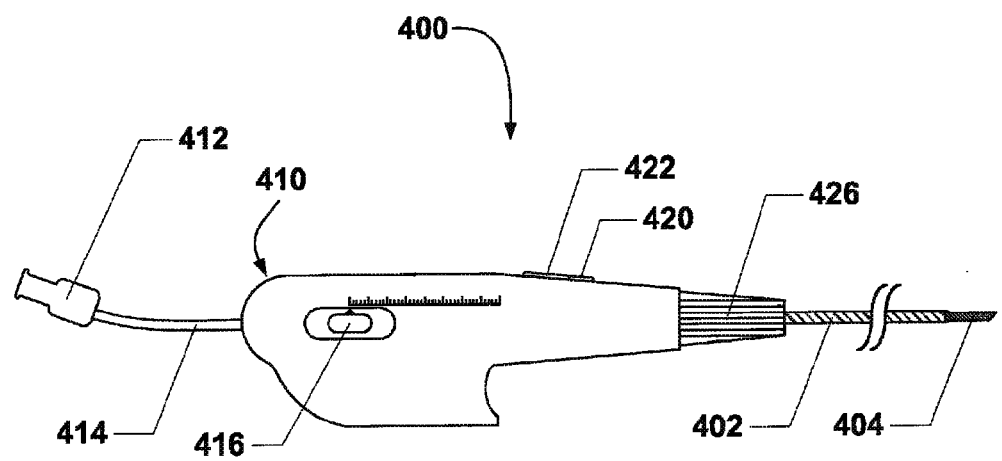
FIG. 15B is a side view of the injection system of FIG. 15A.

Referring now to FIGS. 15A and 15B, the injection system 400 thereshown include an injection cannula 402, an injection needle 404 disposed within the cannula 402, and a proximal handle 410. The injection system further includes a female Luer lock 412 and a connection tube 414. The proximal handle 410 includes a cannula extension controller 416, a maximum needle depth controller 420, a needle injection controller 422, and a torque device 426. As described further above, the proximal handle can be adapted to extend the cannula, advance the injection needle, limit advancement of the injection needle beyond the cannula, and torque the cannula. The use of the maximum needle depth controller 420 and needle injection controller 422 in combination can further prevent perforation of the left ventricular wall and pericardial sac during injection. Mechanical design safeguards operate in combination with real-time echocardiographic guidance to prevent myocardial perforation.

The injection cannula 402 may be formed of a biocompatible superelastic material such as a nickel-titanium (or Nitinol) alloy that can take a curved shape. The cannula size may be between 20 gauge and 24 gauge, more particularly approximately 22 gauge, for example. The distal tip of the cannula can be treated to be echogenic to facilitate ultrasound image guidance. The needle 404 may be formed of stainless steel or a nickel-titanium alloy and may be between 24 gauge and 26 gauge in size. The needle 404 can be treated to be echogenic to facilitate ultrasound image guidance. A multiport manifold (not shown) can be connected to the female Luer lock 412 for delivery of therapeutic solutions, crosslinkable polymer solutions, and other fluids through the injection needle 404.

Figure 16A:
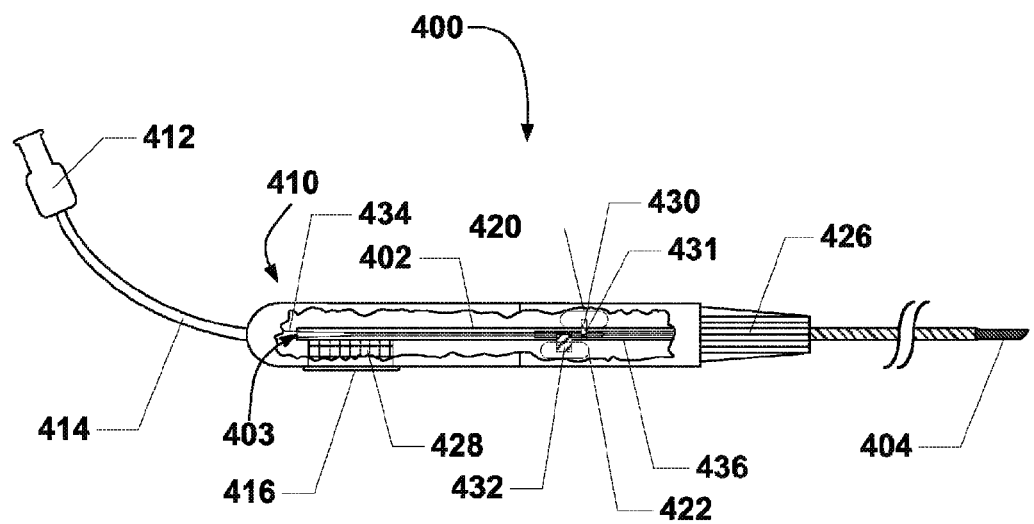
FIG. 16A is another top partial sectional view of injection system FIG. 15A showing the internal elements thereof in greater detail.
Figure 16B:
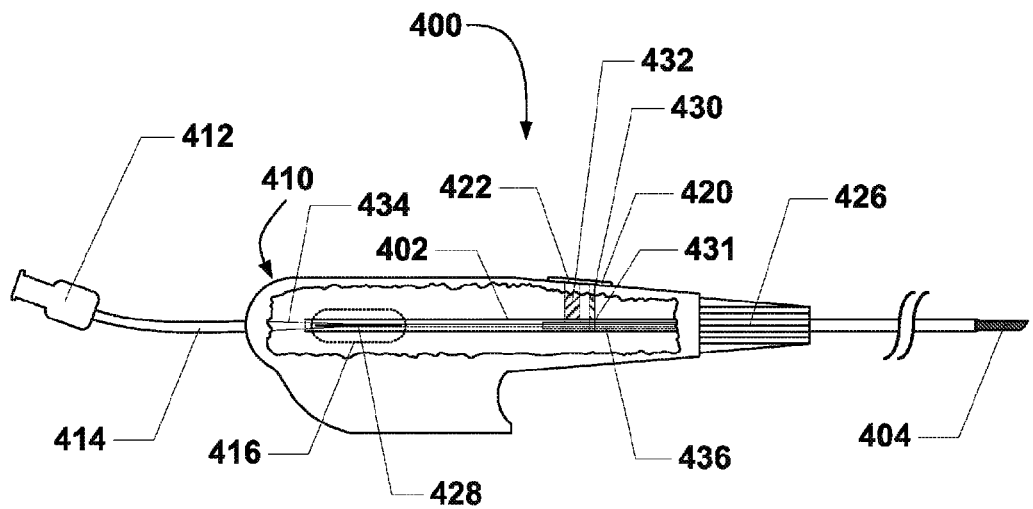
FIG. 16B is a partial sectional side view of the injection system of FIG. 16A.

Referring now to FIGS. 16A and 16B along with FIG. 3, an embodiment of the proximal handle 410 and the internal control mechanisms are illustrated. The segment of the cannula 402 inside the proximal handle 410 is slotted 403. The cannula extension controller 416 is coupled to the cannula 402 by a first rigid member 428. The cannula 402 can be extended beyond the exit port 64 of the injection cannula lumen 62 of the endoventricular injection catheter 2 by sliding the cannula extension controller 416 toward the torque device 426. The maximum needle depth controller 420 is coupled to a stop plate 431 by a second rigid member 430. The needle injection controller 422 is coupled to a needle injection support member 436 by a third rigid member 432. The second and third rigid members 430, 432 extend through the slot 403 of the cannula 402. The needle injection support member 436 extends the length of the cannula and is bonded to the injection needle 404, as for example by welding or brazing. The stop plate 431 is disposed inside the slotted cannula 402 and outside the needle injection support member 436. The maximum length that the injection needle 404 can extend beyond the distal end of the cannula 402 can be limited by the maximum needle depth controller 420. The maximum needle depth controller 420 is used to adjust the distance between the stop plate 431 and the third rigid member 432 that is attached to the needle injection controller 422. The injection needle 404 can be extended beyond the distal end of the injection cannula 402 by sliding the needle injection controller 422 toward the torque device 426. The control mechanisms of the injection system 400, including the cannula extension controller 416, the maximum needle depth controller 420, the needle injection controller 422, and the torque device 426, may be used in combination with real-time echocardiographic guidance to safely inject the needle at a site of interest. Real-time echocardiographic guidance provides visual feedback for primary prevention of myocardial perforation. The maximum needle depth controller 420 provides a proximal mechanical control as a secondary prevention to myocardial perforation. A syringe (not shown) that is filled with a therapeutic agent can be connected to the female Luer lock 412 and used for delivery of the therapeutic agent. The therapeutic agent passes through the connector tube 414, a flexible tube 434, and the injection needle 404 into the myocardium. The profile of the flexible tube 434 tapers from a size comparable to the connector tube 414 down to a size comparable to the injection needle 404.

Figure 17:
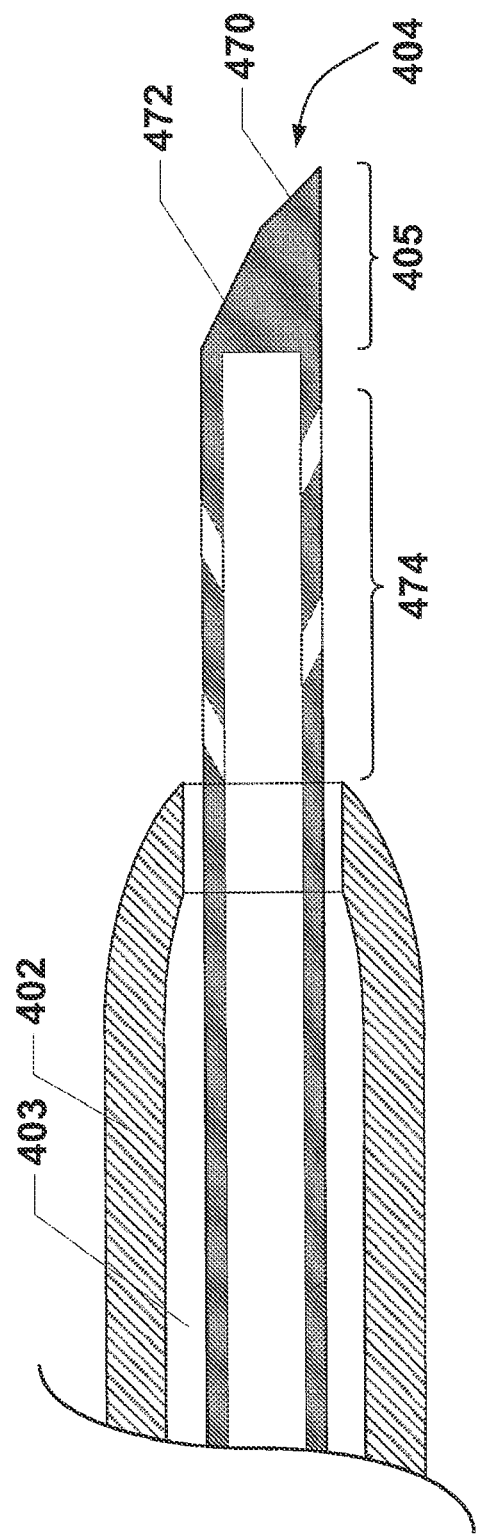
FIG. 17 is a sectional view of the distal tip of an injection cannula and an injection needle with side ports and a closed end according to further aspects of the invention.
Figure 18A:
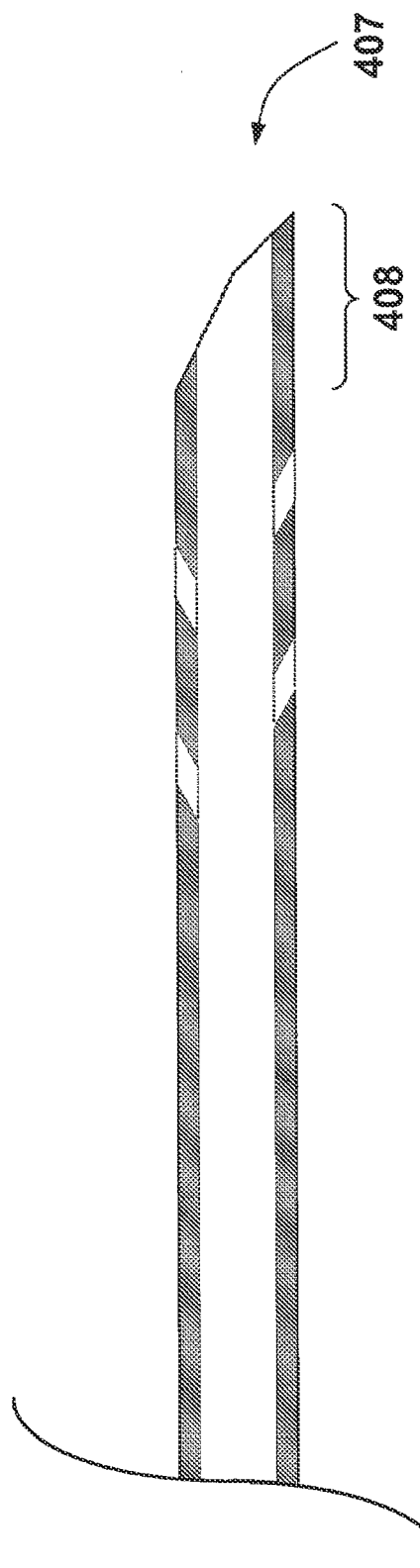
FIG. 18A is a sectional view of the distal tip of another injection needle with side ports and an opened end according to further aspects of the invention.
Figure 18B:
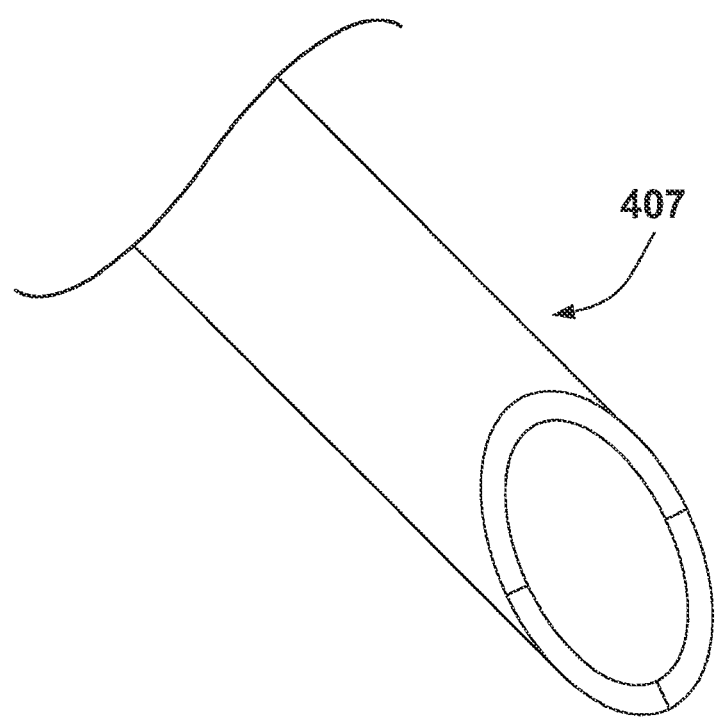
FIG. 18B is a perspective view of the distal tip of an injection needle with an opened end according to further aspects of the invention.

Referring now to FIG. 17, the distal tip of the injection cannula 402 and an embodiment of an injection needle 404 are shown. The needle 404 includes a closed, non-coring tip 405 with a primary bevel 470 and secondary bevel 472. The needle further includes side flush ports 474 to distribute the therapeutic agent. An alternative embodiment of an injection needle 407 is shown in FIGS. 18A and 18B wherein the distal tip 408 of the needle is open.

Figure 19:
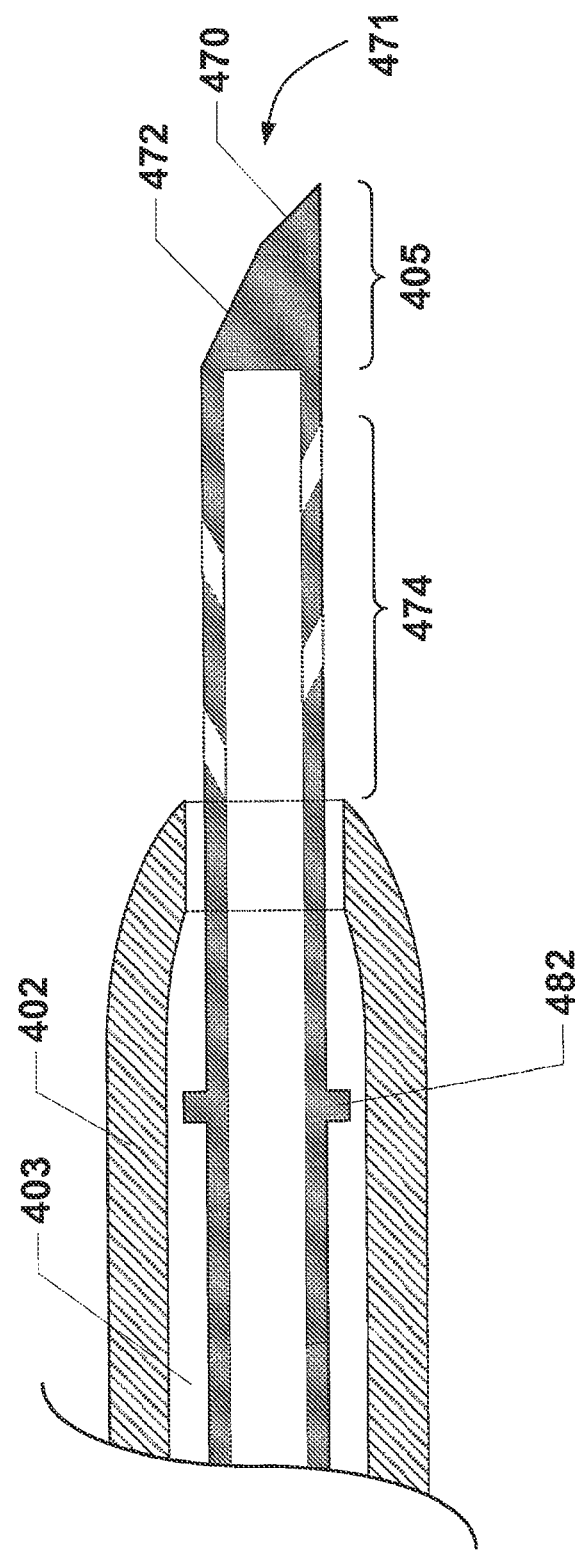
FIG. 19 is a sectional view of the distal tip of an injection cannula and an injection needle with an end stop according to aspects of the invention.

Still another alternative embodiment of the injection needle is shown in FIG. 19 wherein an injection needle 471 comprises an end stop 482. The end stop 482 can be formed by several different methods including swaging or laser welding. The end stop 482 insures that the injection needle does not extend beyond a pre-determined maximum length beyond the cannula, as for example, approximately 6 mm. A maximum depth limiter at the proximal handle of the injection control system may not be sufficient, because the relative longitudinal position of the distal cannula tip and the distal needle tip can shift when traversing a curved path such as the aortic arch. The end stop 482 provides a safeguard in addition to safeguards provided by real-time echocardiographic guidance and a maximum depth limit controller that further mitigates accidental myocardial perforation by the injection needle.

Figure 20:
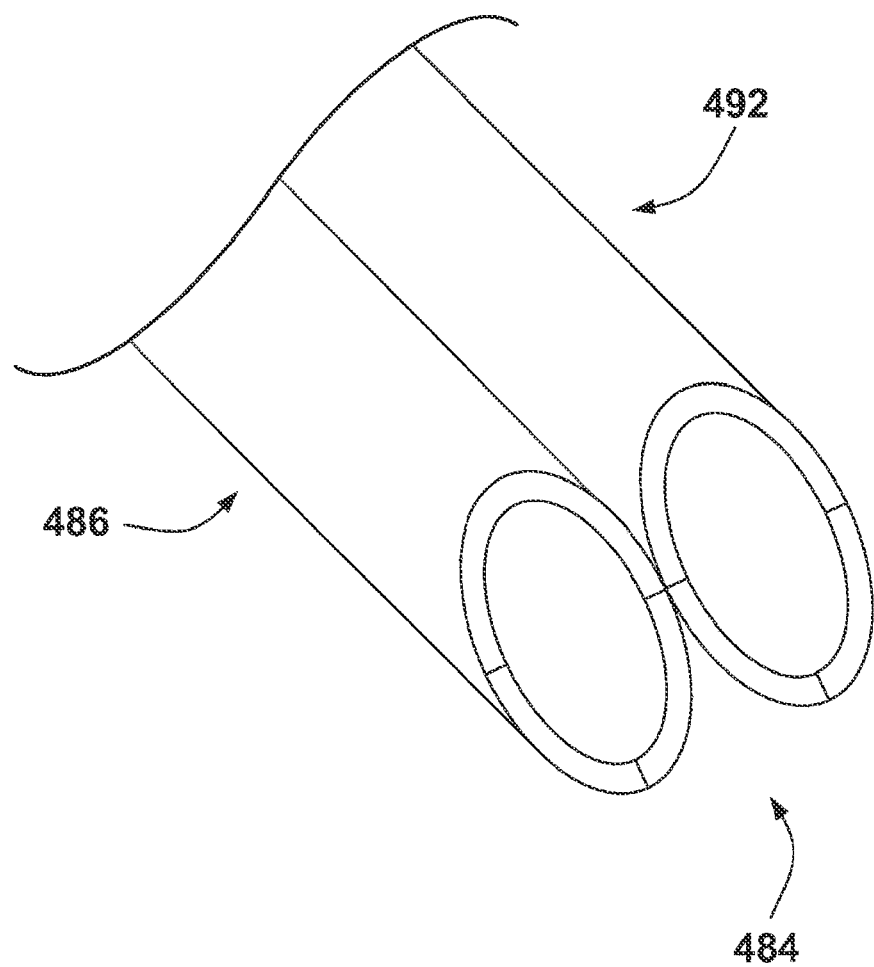
FIG. 20 is a perspective view of the distal tip of an injection needle having a dual injection needle according to further aspects of the invention.

Back leakage of the injected therapeutic agent can reduce the efficacy of the agent. Back leakage can be prevented by injection of a bioabsorbable polymer solution such as a poloxamer that gels as it reaches body temperature. The polymer solution can be administered simultaneously with the injection of the therapeutic solution. Alternatively, the polymer solution can be injected after the injection of the therapeutic agent. The same injection needle can be used for injection of the therapeutic agent and polymer solution. An alternative embodiment of the injection needle may take the form of a dual injection needle 484 as shown in FIG. 20. The first and second needles 486, 492 of the dual injection needle 484 are bonded along a line, as for example by laser welding. The therapeutic agent can be injected using needle 486 while the polymer solution can be injected using needle 492 for example. The dual injection needle 484 may be used in combination with a second connection tube and female Luer lock (not shown) at the injection system proximal handle connected to the second needle.

Figure 21:
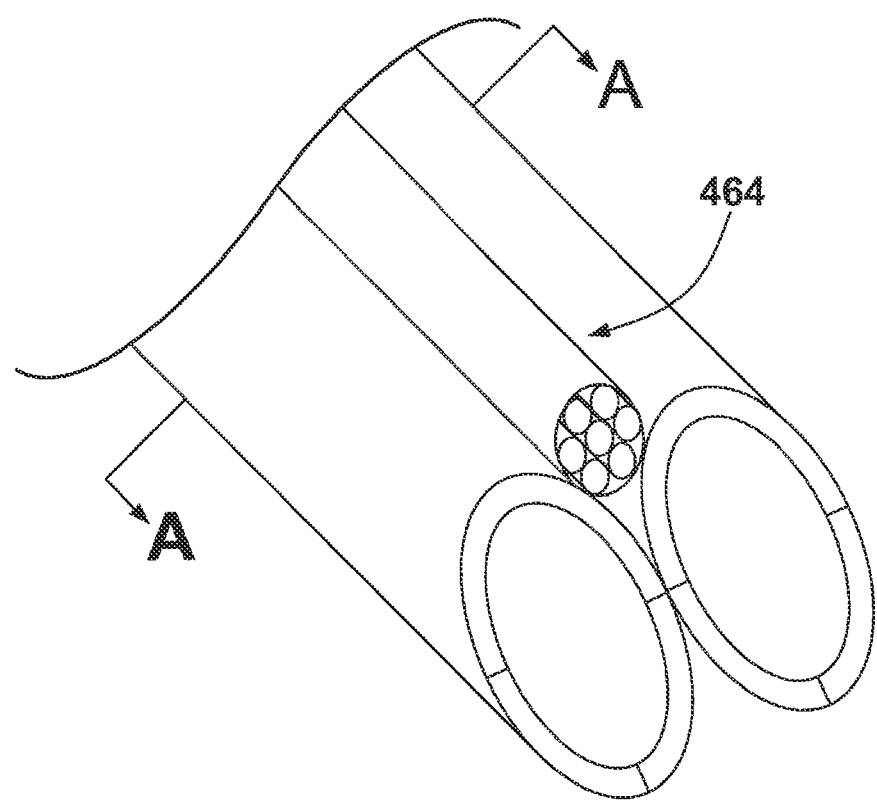
FIG. 21 is a perspective view of the distal tip of a dual injection needle with a fiber optic bundle according to further aspects of the invention.
Figure 21A:
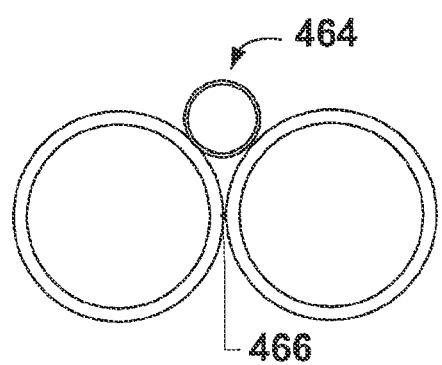
FIG. 21A is a sectional view taken along lines A-A of FIG. 21.

An alternative approach to prevent back leakage of the therapeutic agent is by use of a bioabsorbable photocrosslinkable hydrogel such as poly(ethylene glycol) (or PEG). The photocrosslinkable hydrogel may be administered simultaneously with or secondary to the therapeutic agent. Ultraviolet illumination of the hydrogel at the injection site initiates photocrosslinking and can be performed using a fiber optic bundle 464 as shown in FIGS. 21 and 21A. The fiber optic bundle 464 runs the length of the injection needle and can be disposed above the bond line 466. The proximal end of the fiber optic bundle may be coupled to an ultraviolet light source (not shown) including a lamp providing light having a long wavelength of, for example, 365 nm.

Figure 22:
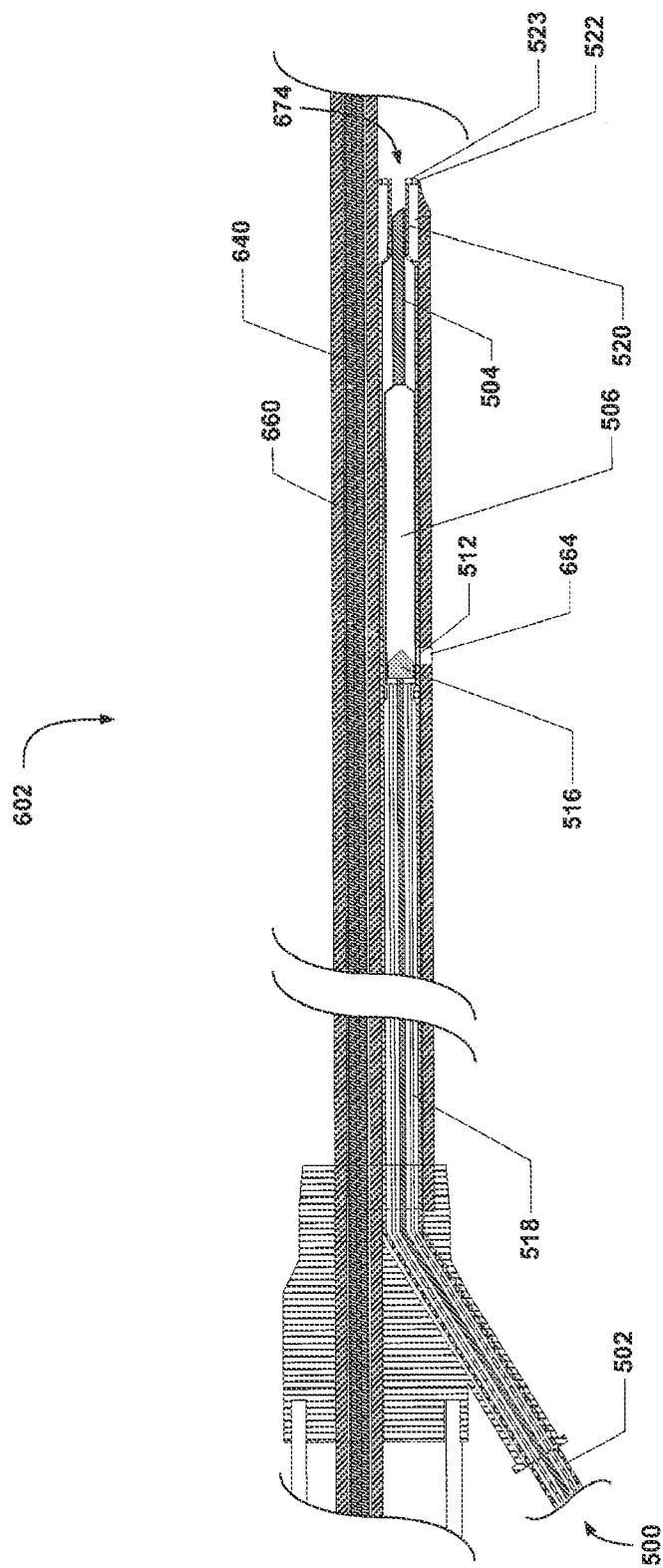
FIG. 22 is a partial sectional view of still another catheter embodying aspects of the invention.

Still another concern regarding delivery of the therapeutic agent to a region of interest is potential trauma to the therapeutic cells during delivery through the injection needle from the proximal end to the distal end such that viability of the therapeutic agent is degraded. An alternative embodiment of an injection system 500 is shown in FIG. 22 wherein the therapeutic agent can be loaded into a distal reservoir chamber 506 to minimize the length of the delivery path. The distal reservoir chamber 506 can be of sufficient volume for multiple injections. The size of a cannula lumen 662 can be increased by reducing the size of the drive cable 640 and imaging core lumen 660. The size of a cannula lumen 662 can be further increased by increasing the catheter profile.

The proximal end of an injection needle 504 is bonded to the reservoir chamber 506. The reservoir chamber can be loaded with the therapeutic agent by retracting the needle to its most proximal position that is determined by a proximal end stop 508 of the cannula 502. When the reservoir chamber is at this loading position a reservoir chamber loading window 510, cannula loading window 512, and a proximal sheath loading window 664 can be aligned to enable loading of the therapeutic agent. The windows 510, 512, 664 may be pass-through holes or holes filled with a self-closing material such as silicone. A plunger 514 and plunger head 516 are advanced distal of the windows to further prevent any leakage of the therapeutic agent outside the reservoir chamber 506.

The cannula 502 comprises a tapered distal section 520 with a flared tip 522. The shoulder 524 of the tapered distal section 520 further prevents the injection needle 504 from extending beyond a pre-determined length, as for example, approximately 6 mm. A distal means to limit extension of the needle beyond the cannula may be necessary in situations wherein the relative longitudinal position of the distal cannula tip and the distal needle tip can shift when traversing a curved path such as the aortic arch. The flared tip 522 provides a blunt surface 523 to help stabilize the cannula against the left ventricular wall and prevent penetration of the cannula into the tissue.

Figure 23A:
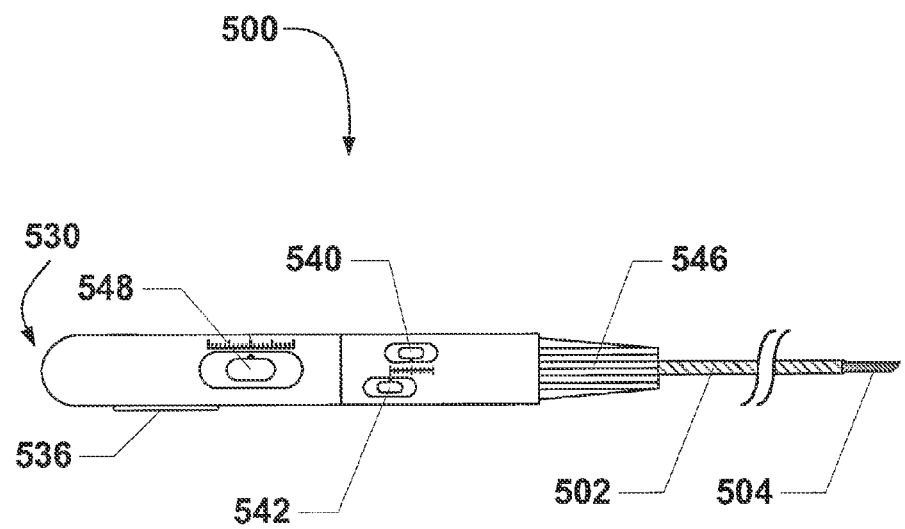
FIG. 23A is a top view of another injection system proximal handle embodying aspects of the invention.
Figure 23B:
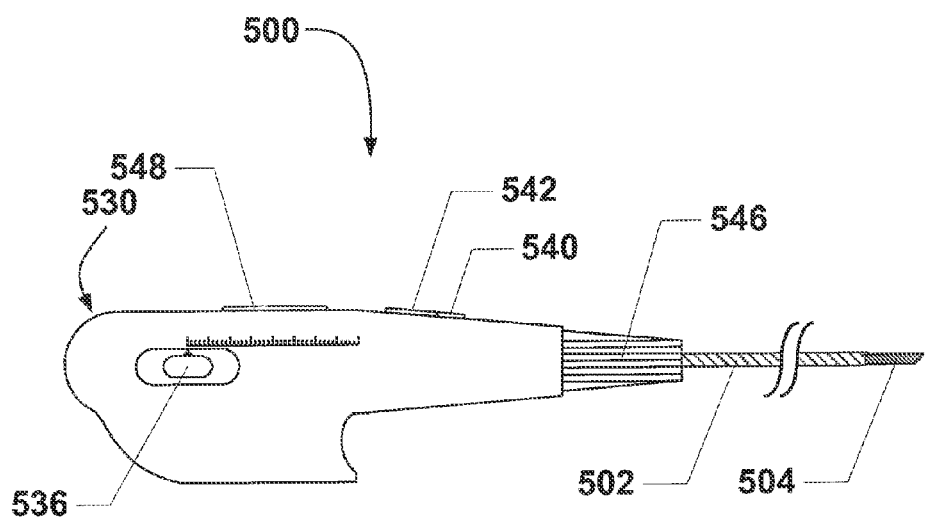
FIG. 23B is a side view of the injection system of FIG. 23A.

Referring now to FIGS. 23A and 23B, a still further injection system 500 includes the injection cannula 502, the injection needle 504 disposed within the injection cannula 502, and a proximal handle 530. The proximal handle 530 comprises a cannula extension controller 536, a maximum needle depth controller 540, a needle injection depth controller 542, a torque device 546, and a distal reservoir plunger controller 548. The maximum needle depth controller 540 is a proximal control to restrict the depth to which the needle 504 can extend beyond the distal tip of the cannula 502. The needle injection depth controller 542 is arranged to vary the position of the needle distal tip relative to the cannula distal tip. The distal reservoir plunger controller 548 is used to dispense the therapeutic agent.

Figure 24A:
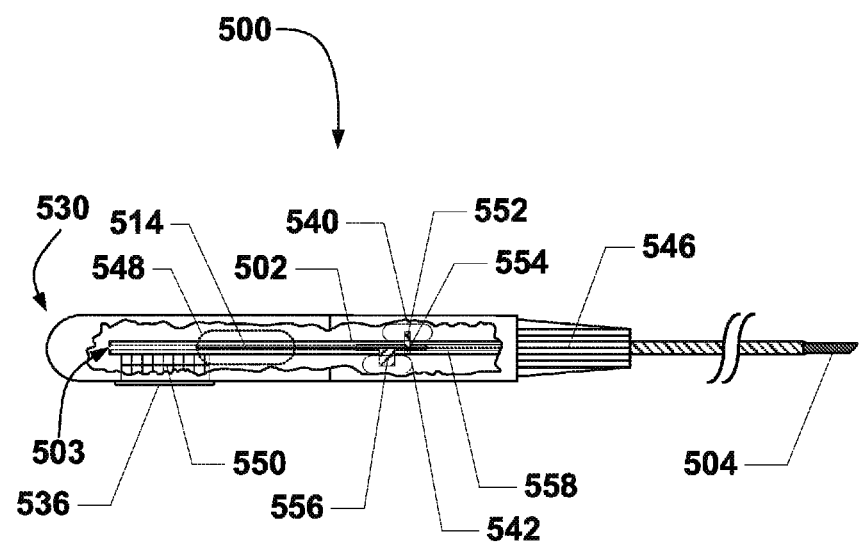
FIG. 24A is another partial sectional top view of the injection system of FIG. 23A showing the internal elements thereof in greater detail.
Figure 24B:
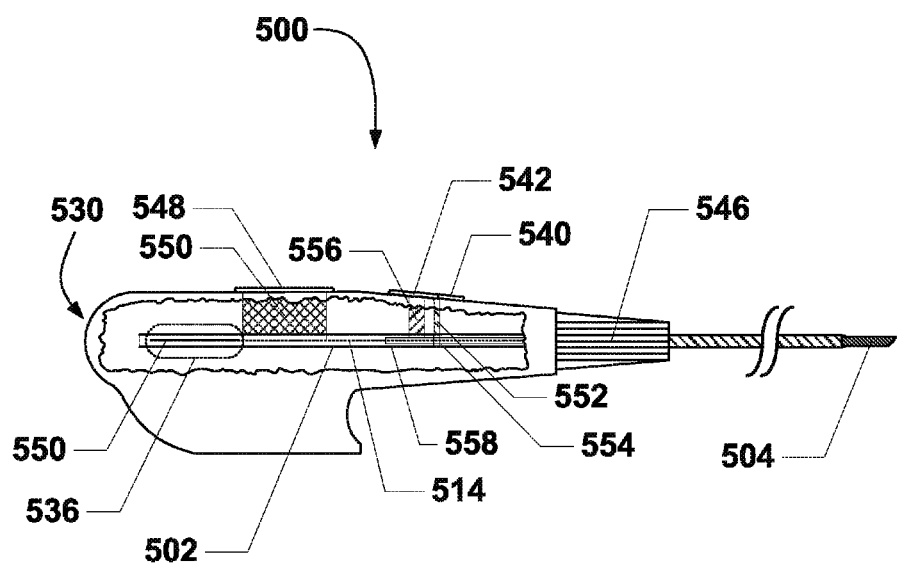
FIG. 24B is a partial sectional side view of the injection system of FIG. 24A.

Referring to FIGS. 24A and 24B along with FIG. 22, the internal control mechanisms of proximal handle 530 are illustrated. The segment of the cannula 502 inside the proximal handle 530 has a slot 503. The cannula extension controller 536 is coupled to the cannula 502 by a first rigid member 550. The cannula 502 can be extended beyond the exit port 674 of the injection cannula lumen 662 of the endoventricular injection catheter 602 by sliding the cannula extension controller 536 toward the torque device 546. The maximum needle depth controller 540 is coupled to a stop plate 554 by a second rigid member 552. The needle injection controller 542 is coupled to a needle injection support member 558 by a third rigid member 556. The distal reservoir plunger controller 548 is coupled to the distal reservoir plunger 514 by a fourth rigid member 550. The second rigid member 552, third rigid member 556, and fourth rigid member 550 extend through the slot 503 of the cannula 502. The needle injection support member 558 extends the length of the cannula 502 and is bonded to the injection needle 504, by welding or brazing, for example. The stop plate 554 is disposed inside the slotted cannula 502 and outside the needle injection support member 558.

The maximum length that the injection needle 504 can extend beyond the distal end of the cannula 502 can be limited by the maximum needle depth controller 540. The maximum needle depth controller 540 is used to adjust the distance between the stop plate 554 and the third rigid member 556 that is attached to the needle injection controller 542. The injection needle 504 can be extended beyond the distal end of the injection cannula 502 by sliding the needle injection controller 542 toward the torque device 546.

The control mechanisms of the injection system 500, including the cannula extension controller 536, the maximum needle depth controller 540, the needle injection controller 542, and the torque device 546 may be used in combination with real-time echocardiographic guidance to safely inject the needle at a site of interest. Real-time echocardiographic guidance provides visual feedback for primary prevention of myocardial perforation. The maximum needle depth controller 540 provides a proximal mechanical control as a secondary prevention to myocardial perforation. The tapered distal section 520 of the cannula 502 provides a distal mechanical control as a tertiary prevention to myocardial perforation. The therapeutic agent can be delivered from the distal reservoir 506 through the needle 504 to the site of interest by use of the distal reservoir plunger controller 548.

Figure 25:
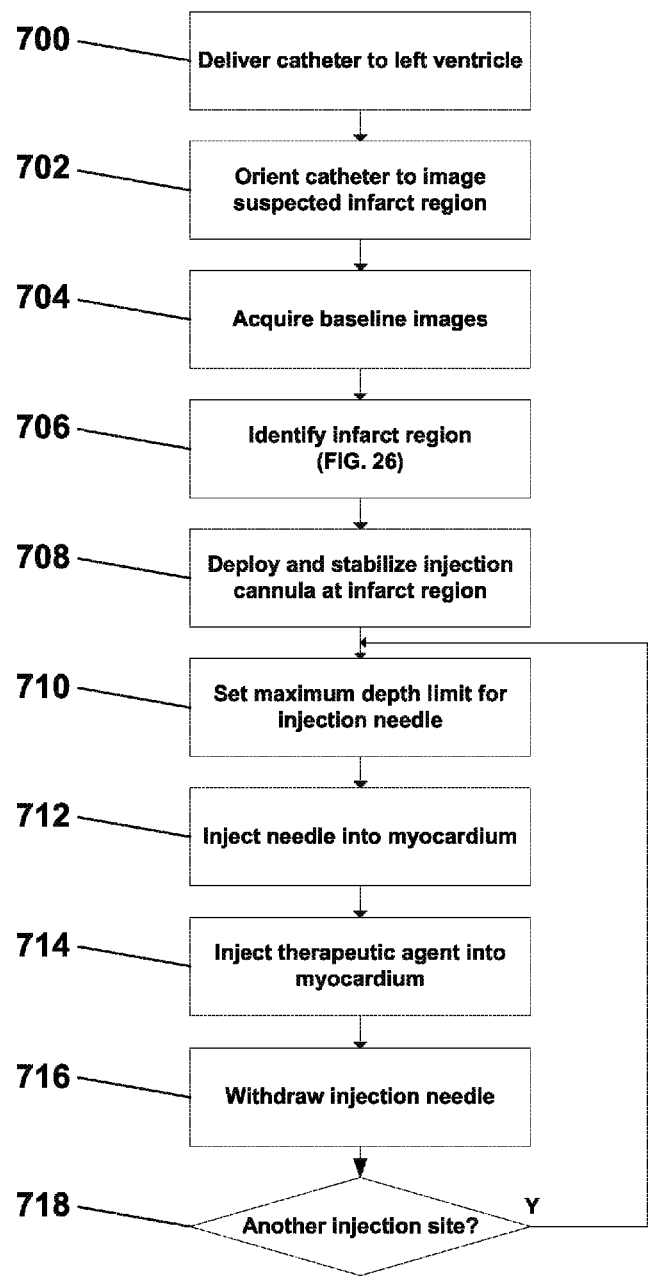
FIG. 25 is a flow diagram illustrating processing stages for image guidance of transendocardial injections according to aspects of the invention.
Figure 26:
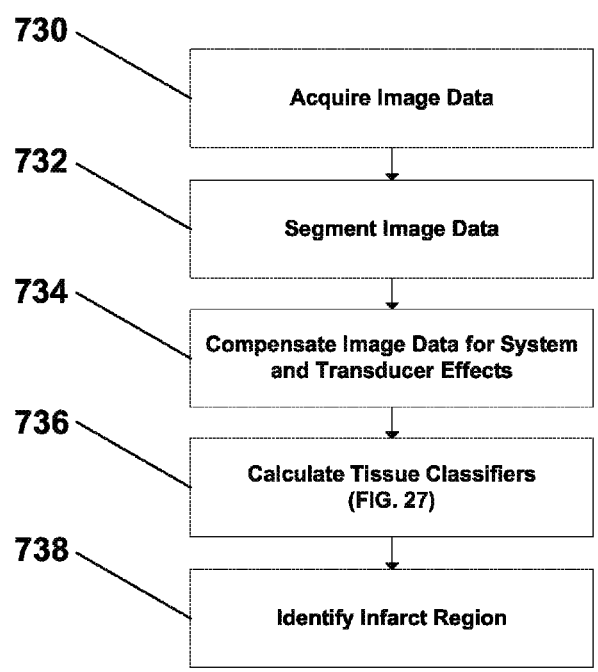
FIG. 26 is a flow diagram illustrating processing stages for identifying an infarct region.
Figure 27:
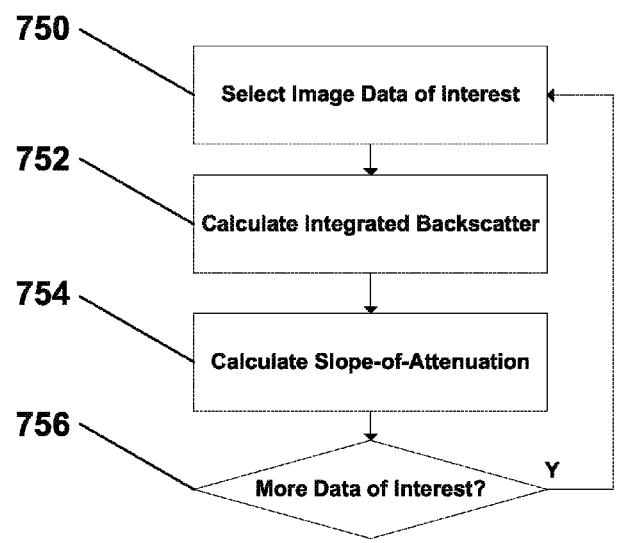
FIG. 27 is a flow diagram illustrating processing stages for calculating tissue classifiers according to further aspects of the invention.

FIGS. 25, 26 and 27 are flow diagrams illustrating sets of processing stages for image guidance of transendocardial injections according to aspects of the invention. FIG. 25 shows an exemplary set of processing stages for transendocardial injection of a therapeutic agent to an infarcted region in a left ventricular wall. The catheter is delivered to the left ventricular chamber in step 700 via a retrograde approach. The catheter is oriented to enable imaging of a region with a suspected infarct in step 702. A set of baseline images are then acquired in step 704.

The region of infarct is identified in step 706. Referring now to FIG. 26, an exemplary set of processing stages to identify an infarct region is illustrated. Image data is first acquired in step 730. Identification of the infarct region includes image segmentation in step 732 into blood and non-blood tissues, compensation of image data for imaging system and ultrasound transducer effects in step 734, calculation of tissue classifiers in step 736, and finally identification of infarct region in step 738. Compensation of system and transducer effects mitigates range-dependent amplitude and frequency variations in the ultrasound signals that can degrade accuracy of tissue classification. FIG. 27 shows an exemplary set of processing stages for calculation of tissue classifiers. The image data of interest are selected 750. The integrated backscatter and slope-of-attenuation tissue parameters are calculated in steps 752 and 754, respectively. Calculation of such tissue classifiers are known to those skilled in the art of ultrasound tissue classification. The process is repeated for all image data of interest as indicated by decision block 756. Referring now to FIG. 26, the calculated tissue classifiers are used to identify the infarct region in step 738. Infarcted tissue is known to have higher values of integrated backscatter and slope-of-attenuation. The ranges of tissue classifiers corresponding to infarcted tissue are determined empirically.

Referring back now to FIG. 25, the injection cannula is deployed and stabilized at the site of infarction in step 708. The maximum depth limit for the injection needle is set in step 710. The needle is then injected into the myocardium in step 712. The therapeutic agent is injected into the myocardium in step 714. The needle is removed from the injection site in step 716 and repositioned at a next injection site following decision block 718 as necessary.

While particular embodiments of the present invention have been shown and described, modifications may be made, and it is therefore intended to cover in the appended claims, all such changes and modifications which fall within the true spirit and scope of the invention as defined by those claims.

What is claimed is:

1. A method of providing image-guided transendocardial injection of a therapeutic agent into a left ventricular wall of a heart, comprising:
providing an endoventricular injection catheter having integrated echocardiographic capability, the endoventricular injection catheter having an elongated body with a first housing, a second housing and a distal section positioned distal to the second housing in a longitudinal direction, the distal section having a distal end and an imaging core and an injection system carried on the elongated body with the imaging core;

providing a telescoping section, the telescoping section including:
- a first supporting member positioned between the first housing and the second housing and being fixedly coupled to the second housing,
- a second member fixedly coupled to the first housing, the second member having a length less than or equal to a length of the first supporting member, and
- a third member supporting a drive cable, the third member and the drive cable extending between the first housing and the distal section, wherein the first supporting member, the second member and the third member are arranged a nested, coaxial arrangement such that one of the first supporting member, second member, and third member nests coaxially within the other two of the first supporting member, second member, and third member, and such that one of the other two of the first supporting member, second member, and third member nests within one of the other two of the first supporting member, second member, and third member;

positioning the endoventricular injection catheter into the left ventricle of the heart, thereby inserting the imaging core into a heart;

transmitting ultrasonic energy via the imaging core;

receiving reflected ultrasonic energy at the distal end;

visualizing the left ventricular wall of the heart using the imaging core;

identifying infarct regions of the left ventricle; and injecting a therapeutic agent into the visualized infarcted regions of the left ventricle using the injection system.

2. The method of claim 1, including the further step of injecting a bioabsorbable agent with the injection system to prevent back flow of the therapeutic agent.

3. The method of claim 1, further comprising moving the telescoping section in a controlled manner to translate the imaging core in the longitudinal direction.

4. The method of claim 1, further comprising limiting a distance of travel of the imaging core between the unextended position and fully-extended position within the length of the second member of the telescoping section.

5. The method of claim 1, wherein the injection system comprises a cannula received by a cannula lumen in the catheter, an injection needle positioned within the cannula, and a proximal handle.

6. The method of claim 5, further comprising
extending the cannula using the proximal handle,
advancing the injection needle,
limiting an extent of advancement of the injection needle beyond the cannula, and torqueing the cannula.

7. The method of claim 5, further comprising controlling the depth to which the injection needle of the injector can extend beyond a distal tip of the cannula.

8. The method of claim 7, further comprising repositioning the injection needle from a first injection site to a second injection site.

9. The method of claim 1, wherein positioning the catheter includes deflecting the distal end of the catheter in a desired direction with one of a steerable guide sheath and a deflection system controlled by a deflection control system.

10. The method of claim 1, wherein identifying the infarct region of the left ventricle comprises
segmenting images into blood and non-blood tissues,
calculating tissue classifiers, wherein tissue classifiers comprises one or more of
integrated backscatter and slope-of-attenuation, and
identifying the infarct region based on calculated tissue classifiers.

11. The method of claim 1, further comprising loading the therapeutic agent into a distal reservoir chamber to minimize a length of a delivery path of the therapeutic agent, wherein the distal reservoir chamber is housed in the distal section.

* * * * *